(12) United States Patent
Becker et al.

(10) Patent No.: US 7,495,093 B2
(45) Date of Patent: *Feb. 24, 2009

(54) AMPLIFICATION AND DETECTION METHOD

(75) Inventors: Michael M. Becker, San Diego, CA (US); Mehrdad R. Majlessi, Escondido, CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/924,910

(22) Filed: Oct. 26, 2007

(65) Prior Publication Data

US 2008/0090246 A1    Apr. 17, 2008

Related U.S. Application Data

(63) Continuation of application No. 09/808,558, filed on Mar. 14, 2001, now Pat. No. 7,399,852, which is a continuation of application No. 09/565,427, filed on May 5, 2000, now Pat. No. 7,070,925, which is a continuation of application No. 08/893,300, filed on Jul. 15, 1997, now Pat. No. 6,130,038.

(60) Provisional application No. 60/021,818, filed on Jul. 16, 1996.

(51) Int. Cl.
    C07H 21/04    (2006.01)
(52) U.S. Cl. .............. 536/24.3; 536/24.31; 536/24.33; 435/6
(58) Field of Classification Search ................ None
    See application file for complete search history.

(56) References Cited

U.S. PATENT DOCUMENTS

| | | | |
|---|---|---|---|
| 4,725,536 A | 2/1988 | Fritsch et al. |
| 4,766,062 A | 8/1988 | Diamond et al. |
| 4,797,355 A | 1/1989 | Stabinsky |
| 4,820,630 A | 4/1989 | Taub |
| 4,822,733 A | 4/1989 | Morrison |
| 4,925,785 A | 5/1990 | Wang et al. |
| 4,996,143 A | 2/1991 | Heller et al. |
| 5,087,558 A | 2/1992 | Webster |
| 5,091,519 A | 2/1992 | Cruickshank |
| 5,118,801 A | 6/1992 | Lizardi et al. |
| 5,210,015 A | 5/1993 | Gelfand et al. |
| 5,403,711 A | 4/1995 | Walder et al. |
| 5,445,933 A | 8/1995 | Eadie et al. |
| 5,487,972 A | 1/1996 | Gelfand et al. |
| 5,514,546 A | 5/1996 | Kool |
| 5,514,551 A | 5/1996 | Yang et al. |
| 5,536,638 A | 7/1996 | Rossau et al. |
| 5,573,906 A | 11/1996 | Bannwarth et al. |
| 5,574,145 A | 11/1996 | Barry et al. |
| 5,607,834 A | 3/1997 | Bagwell |
| 5,641,625 A | 6/1997 | Ecker et al. |
| 5,645,985 A | 7/1997 | Froehler et al. |
| 5,652,099 A | 7/1997 | Conrad |
| 5,656,427 A | 8/1997 | Hammond et al. |
| 5,679,553 A | 10/1997 | Van Gemen et al. |
| 5,691,146 A | 11/1997 | Mayrand |
| 5,723,591 A | 3/1998 | Livak et al. |
| 5,731,148 A | 3/1998 | Becker et al. |
| 5,747,252 A | 5/1998 | Yang et al. |
| 5,808,023 A | 9/1998 | Sanghvi et al. |
| 5,811,533 A | 9/1998 | Gold et al. |
| 5,827,649 A | 10/1998 | Rose et al. |
| 5,837,442 A | 11/1998 | Tsang et al. |
| 5,846,726 A | 12/1998 | Nadeau et al. |
| 5,849,504 A | 12/1998 | Shah et al. |
| 5,866,336 A | 2/1999 | Nazarenko et al. |
| 5,898,031 A | 4/1999 | Crooke et al. |
| 5,914,396 A | 6/1999 | Cook et al. |
| 5,919,630 A | 7/1999 | Nadeau et al. |
| 5,925,517 A | 7/1999 | Tyagi et al. |
| 5,928,862 A | 7/1999 | Morrison |
| 6,001,564 A | 12/1999 | Bergeron et al. |
| 6,020,130 A | 2/2000 | Gold et al. |

(Continued)

FOREIGN PATENT DOCUMENTS

EP    0318245    5/1981

(Continued)

OTHER PUBLICATIONS

Tyagi et al., "Molecular Beacons: Probes that Fluoresce upon Hybridization", *Nature Biotechnology*, vol. 14, p. 303-308, Mar. 1996.

Shimizu et al., "Effects of 5-Methyl Substitution in 2'—O-Methyloligo- (Pyrimidine)Nucleotides on Triple-Helix Formation", Bioorg Med Chem Lett, 1994; 4(8) :1029-32, Elsevier Science Ltd., UK.

Adams et al., "The Biochemistry of the Nucleic Acids," §7.2.1, 259-260 ( 11th ed. 1992).

Barabino et al., "Targeted snRNP Depletion Reveals an Additional Role for Mammalian U1 snRNP in Spliceosome Assembly," Cell, 63:293-302 (1990).

(Continued)

*Primary Examiner*—Heather G Calamita
(74) *Attorney, Agent, or Firm*—Charles B. Cappellari; Carlos A. Fisher

(57) ABSTRACT

The present invention concerns oligonucleotides containing one or more modified nucleotides which increase the binding affinity of the oligonucleotides to target nucleic acids having a complementary nucleotide base sequence. These modified oligonucleotides hybridize to the target sequence at a faster rate than unmodified oligonucleotides having an identical nucleotide base sequence. Such modified oligonucleotides include oligonucleotides containing at least one 2'-O-methylribofuranosyl moiety joined to a nitrogenous base. Oligonucleotides can be modified in accordance with the present invention to preferentially bind RNA targets. The present invention also concerns methods of using these modified oligonucleotides and kits containing the same.

12 Claims, 9 Drawing Sheets

U.S. PATENT DOCUMENTS

| | | | |
|---|---|---|---|
| 6,030,787 | A | 2/2000 | Livak et al. |
| 6,117,635 | A | 9/2000 | Nazarenko et al. |
| 6,130,038 | A * | 10/2000 | Becker et al. ............... 536/24.3 |
| 6,150,097 | A | 11/2000 | Tyagi et al. |
| 6,156,501 | A | 12/2000 | McGall et al. |
| 6,218,107 | B1 | 4/2001 | Brentano et al. |
| 6,410,276 | B1 | 6/2002 | Burg et al. |
| 6,903,206 | B1 | 6/2005 | Becker et al. |
| 7,070,925 | B1 | 7/2006 | Becker et al. |
| 7,399,852 | B2 | 7/2008 | Becker et al. |
| 2005/0106610 | A1 | 5/2005 | Becker et al. |
| 2008/0090247 | A1* | 4/2008 | Becker et al. .................. 435/6 |
| 2008/0114161 | A1 | 5/2008 | Becker et al. |

FOREIGN PATENT DOCUMENTS

| | | |
|---|---|---|
| EP | 0415901 | 3/1991 |
| EP | 0421725 | 4/1991 |
| EP | 0742287 | 11/1996 |
| WO | 9012116 | 10/1990 |
| WO | 9014442 | 11/1990 |
| WO | 9108480 | 6/1991 |
| WO | 9202258 | 2/1992 |
| WO | 9313121 | 7/1993 |
| WO | 94/01550 | 1/1994 |
| WO | 9402501 | 2/1994 |
| WO | 9415169 | 7/1994 |
| WO | 9419023 | 9/1994 |
| WO | 9514706 | 6/1995 |
| WO | 9522623 | 8/1995 |
| WO | 9532305 | 11/1995 |
| WO | 9606950 | 3/1996 |

OTHER PUBLICATIONS

Biencowe et al., "Antisense Probing of the Human U4/U6 snRNP with Biotinylated 2'—OMe RNA Oligonucleotides," Cell, 59:531-539 (1989).

Carmo-Fonseca et al., "In vivo detection of snRNP-rich organelles in the nuclei of mammalian cells," EMBO, 10(7):1863-1873 (1991).

Carmo-Fonseca et al., "Assembly of snRNP-containing Coiled Bodies Is Regulated in Interphase and Mitosis-Evidence . . . Coiled Body Is a Kinetic Nuclear Structure," J.Cell.Biol.,120(4) :841-852(1993).

Carmo-Fonseca et al., "Transcription-dependent Colocalization of the U1, U2, U4/U6 and U5 snRNPs in Coiled Bodies," J.Cell.Biol., 117(1):1-14 (1992).

Carmo-Fonseca et al., "Mammalian nuclei contain foci which are highly enriched in compnnents of the pre-mRNA splicing machinery." EMBO, 10(1):195-206 (1991).

Lamond et al., "Probing the Structure and Function of U2 snRNP with Antisense Oligonucleotides Made of 2'—OMe RNA," Cell , 58:383-390 (1989).

Palfi et al., "Affinity purification of Trypanosoma brucei small nuclear ribonucleoproteins reveals common and specific protein components," Proc.Natl.Acad.Sci.USA, 88:9097-9101 (1991).

Shibahara et al., "Site-directed cleavage of RNA,"Nucl. Acid. Res., 15(11) :4403-4415 (1987).

Sproat et al., "2'-O-Methyloligoribonucleotides:synthesis and applications," from Eckstein, "Oligonucleotides and Analogues: A Practical Approach," Chapter 3, pp. 49-86, (1991).

Wang et al., "Relative stabilities of triple helices composed of combinations of DNA, RNA and 2'—O-methyl-RNA . . . ,"Nucl. Acid. Res., 23(7):1157-1164 (1995).

Winnacker, E.L. , "From Genes To Clones,"VCH Verlagsgesellschaft, Weinheim, FRG, 33-34 (1987).

Wolff et al., "Reconsituted mammalian U4/U6 snRNP complements splicing: a mutational analysis," EMBO, 11(1):345-359 (1992).

Bobst et al., "Effect of the Methylation of the 2'- Hydroxyl Groups in Polyadenylic Acid on its Structure in Weakly Acidic and Neutral Solutions and on its Capability to Form Ordered Complexes with Polyuridylic Acid", J. Mol. Biol., 46:221-234 (1969).

Burd et al., "Conserved Structures and Diversity of Functions of RNA-Binding Proteins", Science, 265:615-621 (1994).

Chiang et al., "Antisense Oligonucleotides Inhibit Intercellular Adhesion Molecule 1 Expression by Two Distinct Mechanisms", J. Biol. Chem., 266(27):18162-18171 (1991).

Corey, "48000-fold Acceleration of Hybridization by Chemically Modified Oligonucleotides", J. Am. Chem. Soc., 117(36):9373-9374 (1995).

Cummins et al., "Characterization of Fully 2'-modified Oligoribonucleotide Hetero- and Homoduplex Hybridization and Nuclease Sensitivity", Nucleic Acids Research, 23(11):2019-2024 (1995).

Dean et al., "Inhibition of Protein Kinase C-α Expression in Human A549 Cells by Antisense Oligonucleotides Inhibits Induction of Intercellular Adhesion Molecule 1 (ICAM-1) mRNA by Phorbol Esters", J. Biol. Chem., 269(23):16416-16426 (1991).

Ecker et al., "Pseudo-Half-Knot Formation with RNA", Science, 257:958-961 (1992).

Goodchild, "Conjugates of Oligonucleotides and Modified Oligonucleotides: A Review of Their Synthesis and Properties", Bioconjugate Chemistry, 1(3) :165-187 (1990).

Hou et al., "Inhibition of tRNA Aminoacylation by 2'—O-Methyl Oligonucleotides", Biochemistry, 35(48) :15340-15348 (1996).

Inoue et al., "Sequence-dependent hydrolysis of RNA using modified oligonucleotide splints and RNase H", FEBS Letter, 215(2) :327-330, 1987.

Inoue et al., "Synthesis and hybridization studies on two complementary nona(2'—O-methyl) ribonucleotides ", Nucleic Acids Research, 15(15) :6131-6148 (1987).

Iribarren et al., "2'—O-Alkyl oligoribonucleotides as antisense probes", Proc. Natl. Acad. Sci, USA, 87:7747-7751 (1990).

Knorre et al., "Oligonucleotdes Linked to Reactive Groups", Oligodeoxynucleotides, Chpt. 8, pp. 173-195, 1989.

Lammond et al "Antisense oligonucleotides made of 2'—O-alkylRNA: their properties and applications in RNA biochemistry", FEBS Letter, 325(1,2) :123-126 (1993).

Leslie et al., "Structure of the Single-stranded Polyribonucleotide Poly(2'—O-methylctidylic Acid)", J. Mol. Biol., 119-399-414 (1978).

Lesnik et al., "Oligodeoxynucleotides Containing 2'—O-Modified Adenosine: Synthesis and Effects on Stability of DNA:RNA Duplexes", Biochemistry, 32(30) :7832-7838 (1993).

Markiewicz et al., "The Modified nucleosides of tRNAs. II. Synthesis of 2'—O-methylcytidylyl (3'—5') cytidine", Nucleic Acids Research, 2(6) :951-960 (1975).

Meinkoth et al., "Hybridization of Nucleic Acids Immobilized on Solid Supports", Analytical Biochemistry, 138:267-284 (1984).

Miller et al., "Effects of a Trinucleotide Ethyl Phosphotriester, $G^m$ p (Et) $G^m$ p (Et) U, on Mammalian Cells in Culture", Biochemistry, 16(9):1988-1996 (1977).

Monia et al, "Evaluation of 2'—Modified Oligonucleotides Containing 2'—Deoxy Gaps as Antisense Inhibitors of Gene Expression", J. Biol. Chem., 268(19) :14514-14522 (1993).

Ohtsuka et al., "Studies on Transfer Ribonucleic Acids and Related Compounds. XLI." Synthesis of tRNA Fragments containing Modified Nucleosides, Chem. Pharm. Bull., 31(2) :513-520 (1983).

Pilet et al., "Structural Parameters of Single and Double Stranded Helical Polyribonucleotides", Biochem. Biophys. Res. Comm., 52(2) :517-523 (1973).

Sproat et al., "Highly efficient chemical synthesis of 2'—O-methyloligoribonucleotides and tetrabiotinylated derivatives; novel probes that are resistant to degradation by RNA or DNA specific nucleases", Nucleic Acids Research, 17(9) :3373-3386 (1989).

Suzuki, "SPKK, a new nucleic acid-binding unit of protein found in histone", EMBO J, 8:797-804 (1989).

Thibaudeau et al., "How Does the Electronegativity of the Substituent Dictate the Strenght of the Gauche Effect?", J. Am. Chem. Soc., 116(9) :4038-4043 (1994).

Wei et al., "Hybridization properties of oligodeoxnucleotide pairs bridged by polyarginine peptides", Nucleic Acids Res., 24(4) :655-661 (1996).

Yamaguchi et al., "Chemical synthesis of the 5'—terminal part bearing cap structure of messenger RNA of cytoplasmic polyhedrosis virus (CPV): m⁷G⁵ ' pppAmpG and m⁷G⁵ 'pppAmpGpU", *Nucleic Acids Res.*, 12(6) :2939-2954 (1984).

"Role of the Ribose 2'—Hydroxyl Groups for the Stabilization of the Ordered Structures of Ribonucleic Acid", *J. Am. Chem. Soc.*, 91(16): 4603-4604 (1969).

Blommers et al., "An approach to the structure determination of nucleic acid analogues hybridized to RNA . . . ," Nucl. Acid. Res., 22(20):4187-4194 (1994).

Boiziau et al., "Antisense 2'—O-alkyl oligoribonucleotides are efficient inhibitors of reverse transcription," Nucl. Acid. Res., 23(1):64-71 (1995).

Bonham et al., "An assesment of the antisense properties of RNase H-competent and steric-blocking oligomers, " Nucl. Acid. Res., 23(7):1197-1203 (1995).

Conrad et al., "Enzymatic synthesis of 2'—modified nucleic acids: identification of important phosphate...,"Nucl. Acid. Res., 23(11):1845-1853 (1995).

Cotten et al., "2'—O-methyl, 2'—O-ethyl oligoribonucleotides and phosphorothioate oligodeoxyribonucleotides . . . ,"Nucl. Acid. Res., 19(10):2629-2635 (1991).

Dominski et al., "Identification and Characterization by Antisense Oligonucleotides of Exon and Intron . . . ,"Mol. Cell. Biol., 14(11):7445-7454 (1994).

Ecker et al., "Rational screening of oligonucleotide combinatorial libraries for drug discovery,"Nucl. Acid. Res., 21(8) :1853-1856 (1993).

Johansson et al., "Target-specific arrest of mRNA translation by antisense 2'—O-alkyloligoribonucleotides,"Nucl. Acid. Res., 22(22) :4591-4598 (1994).

Kawasaki et al., "Synthesis and Biophysical Studies of 2'—dRIBO-2'—F Modified Oligonucleotides," Presentation/Seminar--ISIS Pharmaceuticals (Jan. 1991).

Kean et al., "Interactions of oligonucleotide analogs containing methylphosphonate internucleotide linkages . . . ,"Nucl. Acid. Res., 22(21):4497-4503 (1994).

Keller et al., "Synthesis and hybridization properties of oligonucleotides containing 2'—O-modified ribonucleotides,"Nucl. Acid. Res., 21(19):4499-4505 (1993).

Larrou et al., "RNase H is responsible for the non-specific inhibition of *in vitro* translation by 2'—O-alkyl . . . ,"Nucl. Acid. Res., 23(17) :3434-3440 (1995).

Uhlmann et al., *Chemical Review,* 90(4):558 (1990).

USPTO Office Action, U.S. Appl. No. 08/893,300, filed May 8, 1998.

USPTO Office Action, U.S. Appl. No. 08/893,300, filed Dec. 21, 1998.

USPTO Office Action, U.S. Appl. No. 08/893,300, filed Aug. 4, 1999.

USPTO Notice of Allowance, U.S. Appl. No. 08/893,300, filed Feb. 15, 2000.

PCT Search Report, International Application No. PCT/US97/12347, Apr. 29, 1998.

PCT Written Opinion, International Application No. PCT/US97/12347, Jun. 29, 1998.

PCT Preliminary Examiniation Report, International Application No. PCT/US97/12347, Oct. 12, 1998.

Ullu et al., "2'-O-Methyl RNA Oligonucleotides Identify Two Functional Elements in the Trypanosome Spliced Leader Ribonucleoprotein Particle", J Biol Chem, Jun. 1993, 268(18):13068-73.

"2'-OMe-RNA—The Logical RNA Alternative?," The Glen Report, Jun. 1992, 5(1):1-8, Sterling, Virginia, USA.

* cited by examiner o-diBr-AE o-diMe-AE m-diMe-AE o-MeO-AE o-MeO (cinnamyl)-AE o-Me-AE

SEQUENCE LISTING

<160> NUMBER OF SEQ ID NOS: 11

<210> SEQ ID NO 1
<211> LENGTH: 26
<212> TYPE: DNA
<213> ORGANISM: Escherichia coli

<400> SEQUENCE: 1
atgttgggtt aagtcccgca acgagc                26

<210> SEQ ID NO 2
<211> LENGTH: 26
<212> TYPE: DNA
<213> ORGANISM: Escherichia coli

<400> SEQUENCE: 2
gctcgttgcg ggacttaacc caacat                26

<210> SEQ ID NO 3
<211> LENGTH: 26
<212> TYPE: RNA
<213> ORGANISM: Artificial

```
<220> FEATURE:
<223> OTHER INFORMATION: Escherichia coli target-complementary probe
      sequence
<220> FEATURE:
<221> NAME/KEY: misc_feature
<222> LOCATION: (1)..(26)
<223> OTHER INFORMATION: 2'-O-methyl ribonucleotides

<400> SEQUENCE: 3
gcucguugcg ggacuuaacc caacau                                        26

<210> SEQ ID NO 4
<211> LENGTH: 26
<212> TYPE: DNA
<213> ORGANISM: Artificial
<220> FEATURE:
<223> OTHER INFORMATION: Escherichia coli target-complementary probe
      sequence
<220> FEATURE:
<221> NAME/KEY: misc_feature
<222> LOCATION: (1)..(12)
<223> OTHER INFORMATION: 2'-O-methyl ribonucleotides
<220> FEATURE:
<221> NAME/KEY: misc_feature
<222> LOCATION: (13)..(20)
<223> OTHER INFORMATION: deoxyribonucleotides
<220> FEATURE:
<221> NAME/KEY: misc_feature
<222> LOCATION: (21)..(26)
<223> OTHER INFORMATION: 2'-O-methyl ribonucleotides

<400> SEQUENCE: 4
gcucguugcg ggacttaacc caacau                                        26

<210> SEQ ID NO 5
<211> LENGTH: 26
<212> TYPE: DNA
<213> ORGANISM: Artificial
<220> FEATURE:
<223> OTHER INFORMATION: Escherichia coli target-complementary probe
      sequence
<220> FEATURE:
<221> NAME/KEY: misc_feature
<222> LOCATION: (1)..(12)
<223> OTHER INFORMATION: deoxyribonucleotides
<220> FEATURE:
<221> NAME/KEY: misc_feature
<222> LOCATION: (13)..(20)
<223> OTHER INFORMATION: 2'-O-methyl ribonucleotides
<220> FEATURE:
<221> NAME/KEY: misc_feature
<222> LOCATION: (21)..(26)
<223> OTHER INFORMATION: deoxyribonucleotides

<400> SEQUENCE: 5
gctcgttgcg ggacuuaacc caacat                                        26

<210> SEQ ID NO 6
<211> LENGTH: 26
<212> TYPE: DNA
<213> ORGANISM: Artificial
<220> FEATURE:
<223> OTHER INFORMATION: Escherichia coli target-complementary probe
      sequence
<220> FEATURE:
<221> NAME/KEY: misc_feature
<222> LOCATION: (1)..(8)
<223> OTHER INFORMATION: deoxyribonucleotides
<220> FEATURE:
<221> NAME/KEY: misc_feature
<222> LOCATION: (9)..(24)
<223> OTHER INFORMATION: 2'-O-methyl ribonucleotides
<220> FEATURE:
```

```
<221> NAME/KEY: misc_feature
<222> LOCATION: (25)..(26)
<223> OTHER INFORMATION: deoxyribonucleotides

<400> SEQUENCE: 6
gctcgttgcg ggacuuaacc caacat                                              26

<210> SEQ ID NO 7
<211> LENGTH: 26
<212> TYPE: RNA
<213> ORGANISM: Escherichia coli

<400> SEQUENCE: 7
gcucguugcg ggacuuaacc caacau                                              26

<210> SEQ ID NO 8
<211> LENGTH: 26
<212> TYPE: RNA
<213> ORGANISM: Artificial
<220> FEATURE:
<223> OTHER INFORMATION: Synthetic construct containing base sequence
      present in Escherichia coli
<220> FEATURE:
<221> NAME/KEY: misc_feature
<222> LOCATION: (1)..(26)
<223> OTHER INFORMATION: 2'-O-methyl ribonucleotides

<400> SEQUENCE: 8
auguuggguu aagucccgca acgagc                                              26

<210> SEQ ID NO 9
<211> LENGTH: 26
<212> TYPE: RNA
<213> ORGANISM: Escherichia coli

<400> SEQUENCE: 9
auguuggguu aagucccgca acgagc                                              26

<210> SEQ ID NO 10
<211> LENGTH: 26
<212> TYPE: DNA
<213> ORGANISM: Artificial
<220> FEATURE:
<223> OTHER INFORMATION: Escherichia coli target-complementary probe
      sequence
<220> FEATURE:
<221> NAME/KEY: misc_feature
<222> LOCATION: (1)..(15)
<223> OTHER INFORMATION: deoxyribonucleotides
<220> FEATURE:
<221> NAME/KEY: misc_feature
<222> LOCATION: (16)..(17)
<223> OTHER INFORMATION: 2'-O-methyl ribonucleotides
<220> FEATURE:
<221> NAME/KEY: misc_feature
<222> LOCATION: (18)..(26)
<223> OTHER INFORMATION: deoxyribonucleotides

<400> SEQUENCE: 10
gctcgttgcg ggactuaacc caacat                                              26

<210> SEQ ID NO 11
<211> LENGTH: 26
<212> TYPE: DNA
<213> ORGANISM: Artificial
<220> FEATURE:
<223> OTHER INFORMATION: Escherichia coli target-complementary probe
      sequence
<220> FEATURE:
```

```
<221> NAME/KEY: misc_feature
<222> LOCATION: (1)..(14)
<223> OTHER INFORMATION: deoxyribonucleotides
<220> FEATURE:
<221> NAME/KEY: misc_feature
<222> LOCATION: (15)..(18)
<223> OTHER INFORMATION: 2'-O-methyl ribonucleotides
<220> FEATURE:
<221> NAME/KEY: misc_feature
<222> LOCATION: (19)..(26)
<223> OTHER INFORMATION: deoxyribonucleotides

<400> SEQUENCE: 11
gctcgttgcg ggacuuaacc caacat                                           26
```

AMPLIFICATION AND DETECTION METHOD

CROSS-REFERENCE TO RELATED APPLICATIONS

This application is a continuation of U.S. application Ser. No. 09/808,558, filed Mar. 14, 2001, now U.S. Pat. No. 7,399,852, which is a continuation of U.S. application Ser. No. 09/565,427, filed May 5, 2000, now U.S. Pat. No. 7,070,925, which is a continuation of U.S. application Ser. No. 08/893,300, filed Jul. 15, 1997, now U.S. Pat. No. 6,130,038, which claims the benefit of U.S. Provisional Application No. 60/021,818, filed Jul. 16, 1996, the contents of each of which applications is hereby incorporated by reference herein.

FIELD OF THE INVENTION

This invention pertains to methods and compositions for detecting and amplifying nucleic acid sequences using oligonucleotides which contain one or more nucleotides having a modification or modifications resulting in increased target affinity. Such oligonucleotides have been unexpectedly discovered to hybridize to a target nucleic acid at a significantly greater rate than a corresponding unmodified oligonucleotide hybridizes to the same target. As a result, the methods and compositions of the present invention offer advantages for applications employing nucleic acid hybridization, such as medical and veterinary diagnostics, food testing and forensics.

BACKGROUND OF THE INVENTION

In recent years, nucleic acid hybridization has become an increasingly important means of identifying, measuring and detecting the presence of particular nucleic acids in a given sample. Thus, for example, the fields of medical diagnostics, environmental and food testing, and forensics have all benefitted from the use of nucleic acid hybridization as a rapid, simple and extraordinarily accurate way of testing for the presence or absence of given biological contaminants or microorganisms in a sample.

Most nucleic acid hybridization schemes have features in common. One such typical feature is the use of single-stranded nucleic acid probes (or denatured double-stranded probes) having a defined or known nucleotide sequence. Probe molecules may be derived from biological sources, such as genomic DNA or RNA, or may be enzymatically synthesized, either in a prokaryotic or eukaryotic host cell or in vitro. Presently, most nucleic acid probes in common use are oligonucleotide probes made using chemical synthetic methods ("synthetic oligonucleotides"). One such synthetic method is automated sequential addition of 3'-activated, protected nucleotides to the 5' end of a growing, solid phase-bound oligonucleotide chain, followed by cleavage of the completed oligonucleotide from the support and deprotection. See, e.g., Eckstein, *Oligonucleotides & Analogues: A Practical Approach* (1991).

Synthetic oligonucleotides for use as hybridization probes are typically deoxyribonucleotides having a nucleotide sequence complementary to a nucleotide sequence of the nucleic acid to be detected. DNA oligonucleotides are classically preferred for a number of reasons. Among these is the greater stability DNA has to enzymatic hydrolysis upon exposure to common samples, due to the almost ubiquitous presence in samples of various RNAses. RNA is also known to be less chemically stable than DNA, e.g., RNA degradation is facilitated by the presence of base, heavy metals. And compared to RNA, DNA is less prone to assume stable secondary structures under assay conditions. Such secondary structures can render oligonucleotides unavailable for inter-molecular hybridization. Nevertheless, RNA oligonucleotides may be used, even though they are less preferred.

Nucleic acid hybridization exploits the ability of single-stranded nucleic acids to form stable hybrids with corresponding regions of nucleic acid strands having complementary nucleotide sequences. Such hybrids usually consist of double-stranded duplexes, although triple-stranded structures are also known. Generally speaking, single-strands of DNA or RNA are formed from nucleotides containing the bases adenine (A), cytosine (C), thymidine (T), guanine (G), uracil (U), or inosine (I). The single-stranded chains may hybridize to form a double-stranded structure held together by hydrogen bonds between pairs of complementary bases. Generally, A is hydrogen bonded to T or U, while G or I is hydrogen bonded to C. Along the double-stranded chain, classical base pairs of AT or AU, TA or UA, GC, or CG are present Additionally, some mismatched base pairs (e.g., AG, GU) may be present. Under appropriate hybridization conditions, DNA/DNA, RNA/DNA, or RNA/RNA hybrids can form.

By "complementary" is meant that the nucleotide sequences of corresponding regions of two single-stranded nucleic acids, or two different regions of the same single-stranded nucleic acid, have a nucleotide base composition that allows the single strands to hybridize together in a stable double-stranded hydrogen-bonded region under stringent hybridization conditions. When a contiguous sequence of nucleotides of one single stranded region is able to form a series of "canonical" hydrogen-bonded base pairs with an analogous sequence of nucleotides of the other single-stranded region, such that A is paired with U or T, and C is paired with 0, the nucleotides sequences are "perfectly" complementary.

The extreme specificity of nucleic acid hybridization, which under some circumstances can allow the discrimination of nucleic acids differing by as little as one base, has allowed the development of hybridization-based assays of samples containing specific microorganisms, nucleic acids bearing given genetic markers, tissue, biological fluids and the like. Such assays are often able to identify nucleic acids belonging to particular species of microorganisms in a sample containing other, closely-related species. Nucleic acid hybridization assays can also specifically detect or identify certain individuals, or groups of individuals, within a species, such as in the forensic use of RFLP (restriction fragment length polymorphism) and PCR (polymerase chain reaction) testing of samples of human origin.

The use of oligonucleotides as a diagnostic tool in nucleic acid hybridization testing often involves, but need not involve, the use of a reporting group or "label" which is joined to the oligonucleotide probe molecule, or both the probe and the target. Such a reporter group moiety may include, for example, a radioisotope, chemiluminescent or fluorescent agent, or enzyme joined to the oligonucleotide. The label is employed to render the probe capable of detection, particularly when the probe is hybridized to the target nucleic acid.

The majority of assay methods employing nucleic acids utilize a physical separation step in order to separate the probe:analyte hybrid from unbound probe. These assay methods are called "heterogeneous" assays. In nucleic acid hybridization assays, an analyte molecule is the target nucleic acid species sought to be detected, quantitated and/or identified. A "hybrid" is a partly or wholly double-stranded nucleic acid comprising two single-stranded nucleic acids, such as a probe and a target nucleic acid, having a region of complementarity resulting in intermolecular hydrogen bonding under assay and/or amplification conditions.

Assay methods utilizing a physical separation step include methods employing a solid-phase matrix, such as glass, minerals or polymeric materials, in the separation process. The separation may involve preferentially binding the probe:analyte complex to the solid phase matrix, while allowing the unassociated probe molecules to remain in a liquid phase. Such binding may be non-specific, as, for example, in the case of hydroxyapatite, or specific, for example, through sequence-specific interaction of the target nucleic acid with a "capture" probe which is directly or indirectly immobilized on the solid support. In any such case, the amount of probe remaining bound to the solid phase support after a washing step is proportional to the amount of analyte in the sample.

Alternatively, the assay may involve preferentially binding the unhybridized probe while leaving the hybrid to remain in the liquid phase. In this case the amount of probe in the liquid phase after a washing step is proportional to the amount of analyte in the original sample. When the probe is a nucleic acid or oligonucleotide, the solid support can include, without limitation, an adsorbent such as hydroxyapatite, a polycationic moiety, a hydrophobic or "reverse phase" material, an ion-exchange matrix, such as DEAE, a gel filtration matrix, or a combination of one or more of these solid phase materials. The solid support may contain one or more oligonucleotides, or other specific binding moiety, to capture, directly or indirectly, probe, target, or both. In the case of media, such as gel filtration, polyacrylamide gel or agarose gel, the separation is not due to binding of the oligonucleotide but is caused by molecular sieving of differently sized or shaped molecules. In the latter two cases, separation may be driven electrophoretically by application of an electrical current through the gel causing the differential migration through the gel of nucleic acids of different sizes or shapes, such as double-stranded and single-stranded nucleic acids.

A heterogeneous assay method may also involve binding the probe to a solid-phase matrix prior to addition of a sample suspected of containing the analyte of interest. The sample can be contacted with the label under conditions which would cause the desired nucleic acid to be labeled, if present in the sample mixture. The solid phase matrix may be derivatized or activated so that a covalent bond is formed between the probe and the matrix. Alternatively, the probe may be bound to the matrix through strong non-covalent interactions, including, without limitation, the following interactions: ionic, hydrophobic, reverse-phase, immunobinding, chelating, and enzyme-substrate. After the matrix-bound probe is exposed to the labeled nucleic acid under conditions allowing the formation of a hybrid, the separation step is accomplished by washing the solid-phase matrix free of any unbound, labeled analyte. Conversely, the analyte can be bound to the solid phase matrix and contacted with labeled probe, with the excess free probe washed from the matrix before detection of the label.

Yet another type of assay system is termed "homogeneous assay." Homogenous assays can generally take place in solution, without a solid phase separation step, and commonly exploit chemical differences between the free probe and the analyte:probe complex. An example of an assay system which can be used in a homogenous or heterogeneous format is the hybridization protection assay (HPA) disclosed in Arnold et al., U.S. Pat. No. 5,283,174, the contents of which are hereby incorporated by reference herein. In HPA, a probe is linked to a chemiluminescent moiety, contacted with an analyte and then subjected to selective chemical degradation or a detectable change in stability under conditions which alter the chemiluminescent reagent bound or joined to unhybridized probe, without altering the chemiluminescent reagent bound or joined to an analyte:probe conjugate. Subsequent initiation of a chemiluminescent reaction causes the hybrid-associated label to emit light.

Competition assays, in which a labeled probe or analyte competes for binding with its unlabeled analog, are also commonly used in a heterogeneous format. Depending on how the system is designed, either the amount of bound, labeled probe or the amount of unbound, labeled probe can be correlated with the amount of analyte in a sample. However, such an assay can also be used in a homogeneous format without a physical separation step, or in a format incorporating elements of both a homogeneous and a heterogeneous assay.

The assay methods described herein are merely illustrative and should not be understood as exhausting the assay formats employing nucleic acids known to those of skill in the art.

Nucleic acid hybridization has been utilized in methods aimed at using oligonucleotides as therapeutic agents to modify or inhibit gene expression within living organisms. In an example of such utilization, oligonucleotide "antisense" agents can be targeted specifically to an mRNA species encoding a deleterious gene product, such as a viral protein or an oncogene. See, e.g., Zamecnik et al., 75 Proc. Nat'l. Acad. Sci. (USA), 280-284 (1978); Stephenson et al., 75 Proc. Nat'l. Acad. Sci. (USA), 285-288 (1978); and Tullis, U.S. Pat. No. 5,023,243. Although Applicant does not wish to be bound by theory, it is thought that the RNA:DNA duplex which results from the binding of the antisense oligonucleotide to RNA targets may serve as a substrate for RNAse H, an RNA-degrading enzyme present in most cells and specific for DNA contained in an RNA:DNA duplex. According to this model, the target RNA molecule is destroyed through hybridization to the antisense oligonucleotide. Variations of this general strategy exist, wherein, for example, the oligonucleotide has a structure conferring an enzymatic activity on the oligonucleotide, such as the RNAse activity of so-called ribozymes. See, e.g., Goodchild, International Publication No. WO 93/15194.

Because therapeutic antisense oligonucleotides are primarily designed to function in vivo, formulations for the delivery of such agents must not significantly inhibit normal cellular function. Thus, nuclease inhibitors, which can sometimes be included in in vitro diagnostic tests to prevent oligonucleotide degradation, are not suitable for use in vivo. This fact has resulted in the design of various oligonucleotides modified at the internucleotide linkage, at the base or sugar moieties, or at combinations of these sites to have greater nuclease resistance than unmodified DNA.

Thus, a number of oligonucleotide derivatives have been made having modifications at the nitrogenous base, including replacement of the amino group at the 6 position of adenosine by hydrogen to yield purine; substitution of the 6-keto oxygen of guanosine with hydrogen to yield 2-amino purine, or with sulphur to yield 6-thioguanosine, and replacement of the 4-keto oxygen of thymidine with either sulphur or hydrogen to yield, respectively, 4-thiothymidine or 4-hydrothymidine. All these nucleotide analogues can be used as reactants for the synthesis of oligonucleotides. See, e.g., *Oligonucleotides and Analogues: A Practical Approach*, supra. Other substituted bases are known in the art. See, e.g., Cook et al, International Publication No. WO 92/02258, entitled "Nuclease Resistant, Pyrimidine Modified Oligonucleotides that Detect and Modulate Gene Expression," which is incorporated by reference herein. Base-modified nucleotide derivatives can be commercially obtained for oligonucleotide synthesis.

Similarly, a number of nucleotide derivatives have been reported having modifications of the ribofuranosyl or deoxyribofuranosyl moiety. See, e.g., Cook et al, International Publication No. WO 94/19023, entitled "Cyclobutyl Antisense Oligonucleotides, Methods of Making and Use Thereof"; McGee et al., International Publication No. WO 94/02501, entitled "Novel 2'-O-Alkyl Nucleosides and Phosphoramidites Processes for the Preparation and Uses Thereof"; and Cook, International Publication No. WO 93/13121, entitled "Gapped 2'-modified Oligonucleotides." Each of these publications is hereby incorporated by reference herein.

Most oligonucleotides comprising such modified bases have been formulated with increased cellular uptake, nuclease resistance, and/or increased substrate binding in mind. In other words, such oligonucleotides are described as therapeutic gene-modulating agents.

Nucleic acids having modified nucleotide residues exist in nature. Thus, depending on the type or source, modified bases in RNA can include methylated or dimethylated bases, deaminated bases, carboxylated bases, thiolated bases and bases having various combinations of these modifications. Additionally, 2'-O-alkylated bases are known to be present in naturally occurring nucleic acids. See, ADAMS, THE BIOCHEMISTRY OF THE NUCLEIC ACIDS, 7,8 (11$^{th}$ ed. 1993).

SUMMARY OF THE INVENTION

This invention concerns diagnostic methods and compositions employing nucleic acid hybridization techniques. Applicant has surprisingly discovered that oligonucleotides, comprised of one or more modified nucleotides, which have increased binding affinity to a target nucleic acid having a complementary nucleotide sequence, will hybridize to the target nucleic acid at a faster rate than unmodified oligonucleotides. The inventions described herein are drawn to the use of oligonucleotides, wholly or partially so modified, in methods involving their use as, for example, hybridization assay probes, amplification primers, helper oligonucleotides, and oligonucleotides for the capture and immobilization of desired nucleic acids.

Although the present invention is not to be seen as so limited, in particularly preferred embodiments the present invention concerns diagnostic methods utilizing oligonucleotides having nucleotides with 2' modifications to their ribofuranosyl (or deoxyribofuranosyl) moieties. In particular, Applicant has discovered that incorporating nucleotides having such modifications as part of synthetic oligonucleotides can profoundly increase the rate of nucleic acid hybridization, and the preferential binding of such oligonucleotides, to RNA targets over DNA targets. A currently preferred embodiment makes use of oligonucleotides containing nucleotide analogues having 2'-O-methylribofuranosyl moieties linked to a nitrogenous base. Other substitutions at the 2' position of the sugar would be expected, in light of the present disclosure, to have similar properties so long as the substitution is not so large as to cause steric inhibition of hybridization. Additionally, in light of the discoveries giving rise to the present invention, other modifications which increase the $T_m$ of a modified oligonucleotide:target hybrid would reasonably be expected to contribute to increases in the rate of hybridization as well. Such modifications may occur at the 2' position (or other positions) of the deoxyribofuranosyl or ribofuranosyl moiety (such as 2' halide substitutions), on the nitrogenous bases (such as N-diisobutylaminomethylidene-5-(1-propynyl)-2'-deoxycytidine; a cytidine analog, or 5-(1-propynyl)-2'-deoxyuridine); a thymidine analog, or in the linkage moiety. Thus, while specific reference is made throughout this application to 2' modifications, those of skill in the art will understand that other modifications leading to an increased $T_m$ of a modified oligonucleotide:target hybrid over a hybrid containing an unmodified oligonucleotide of identical base sequence would be expected to have similar properties and effects on hybridization kinetics.

While the term $T_m$ refers to the temperature at which 50% of a population of equal amounts of complementary nucleic acid strands are in the double-stranded form, throughout this disclosure the "$T_m$ of an oligonucleotide" or a nucleic acid (single-stranded) is intended to mean the $T_m$ of an oligonucleotide or nucleic acid in a nucleic acid duplex with a target, wherein the nucleic acid contains a base sequence region which is exactly complementary to a base sequence region of the oligonucleotide, unless otherwise indicated.

Because the $T_m$ of the modified oligonucleotides is higher than that of corresponding, unmodified oligonucleotides of the same base sequence, the compositions and diagnostic methods described herein enable the use of oligonucleotides and oligonucleotide probes of shorter length than are otherwise practical for the specific hybridization and detection of nucleic acid targets (preferably RNA targets). The use of shorter oligonucleotides to specifically bind to target nucleic acids at a given temperature has additional advantages. For instance, shorter oligonucleotides will generally have a greater ability to discriminate perfectly complementary targets from "mismatched" base sequence regions. Shorter oligonucleotides are also less likely to overlap undesirable base sequences. Additionally, because of the higher $T_m$, the modified oligonucleotides can stably hybridize at higher temperatures than their unmodified counterparts.

The use of higher hybridization temperatures kinetically drives the hybridization reaction, resulting in faster hybridization rates than would occur at lower temperatures. Further, the modified oligonucleotides used in the methods of the present invention result in faster hybridization rates than the unmodified versions, even when the temperature is not raised.

An increased hybridization rate leads to several other advantages in diagnostic assays. For example, diagnostic assays conducted in accordance with the present invention can be conducted more rapidly than in previously existing hybridization assays. In cases in which the results of the assay may dictate a course of medical treatment or other action, a faster assay result has clear prognostic advantages and may result in more effective treatment. Also, owing to faster hybridization rates and greater affinity of modified oligonucleotides for targets, especially RNA targets, lower concentrations of probe may be used to achieve the same amount of signal. Thus, the assay background (or "noise") can be reduced and the lower concentration of probe can help eliminate undesirable cross-reactions with non-target nucleic acids. Additionally, these assays may be run in larger volumes of sample, thus increasing the sensitivity of the assay.

Thus, hybridization assay probes, amplification oligonucleotides, sample preparation oligonucleotides and/or helper oligonucleotides can all be designed to contain modified bases which have the advantage of increasing the rate of target-specific hybridization.

DETAILED DESCRIPTION OF THE INVENTION

Definitions

Figure 1A:
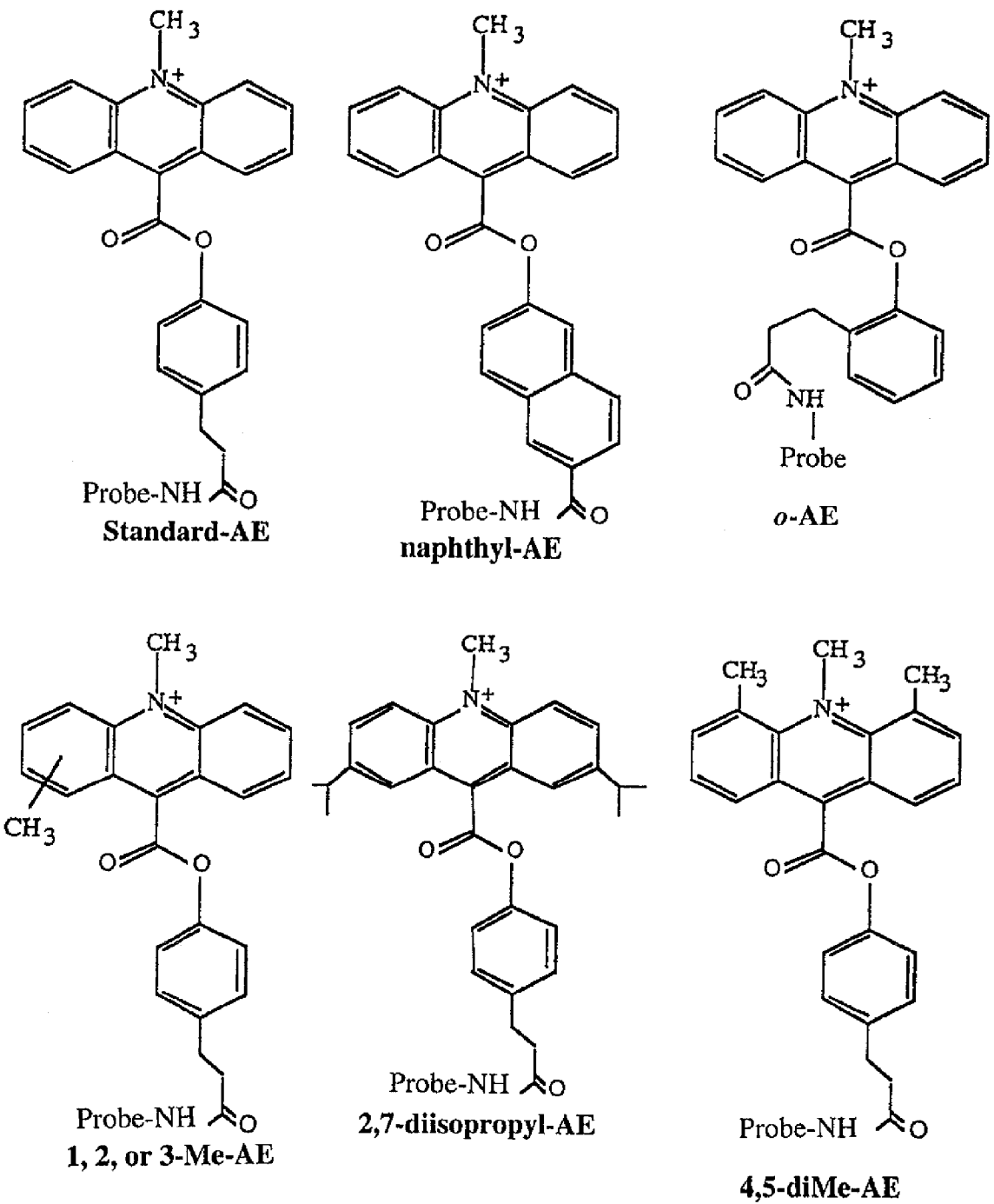
FIGS. 1A-C provide the IUPAC nomenclature for a sampling of acridinium esters that may be used as detectable chemiluminescent labels in the present disclosure.
Figure 1B:
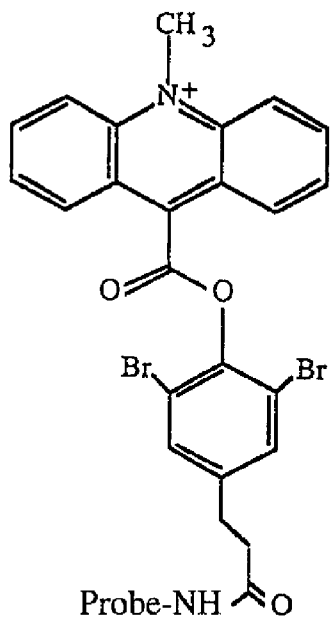
Figure 1B:
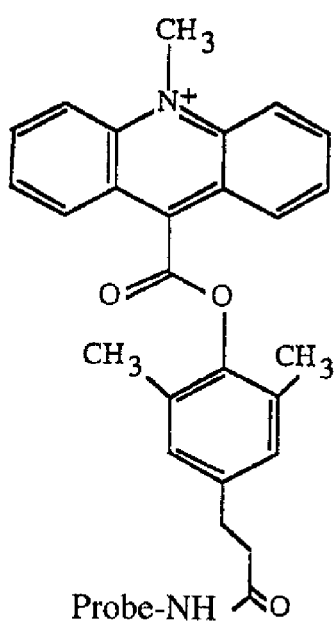
Figure 1B:
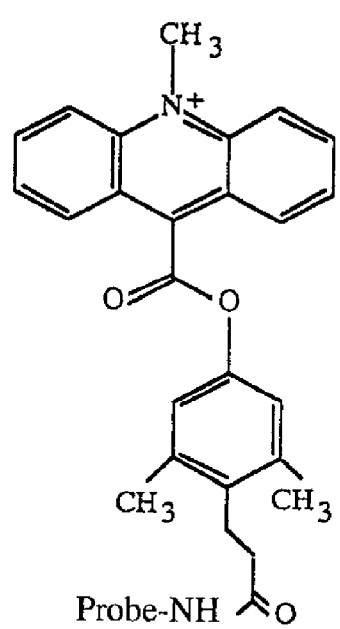
Figure 1B:
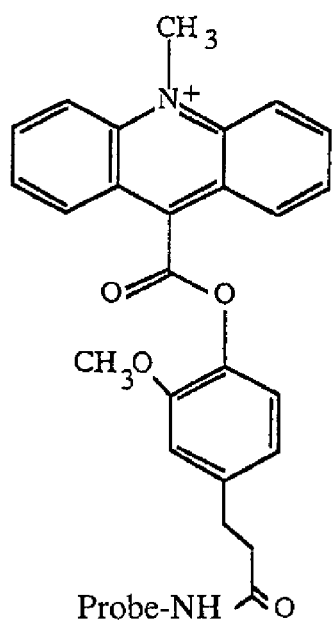
Figure 1B:
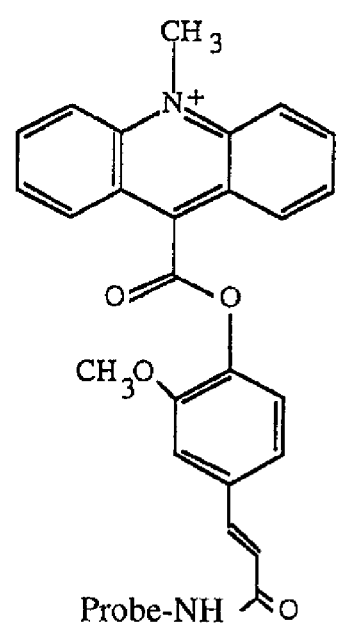
Figure 1B:
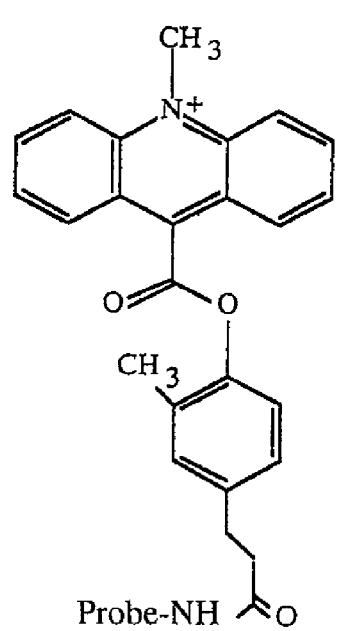
Figure 1C:
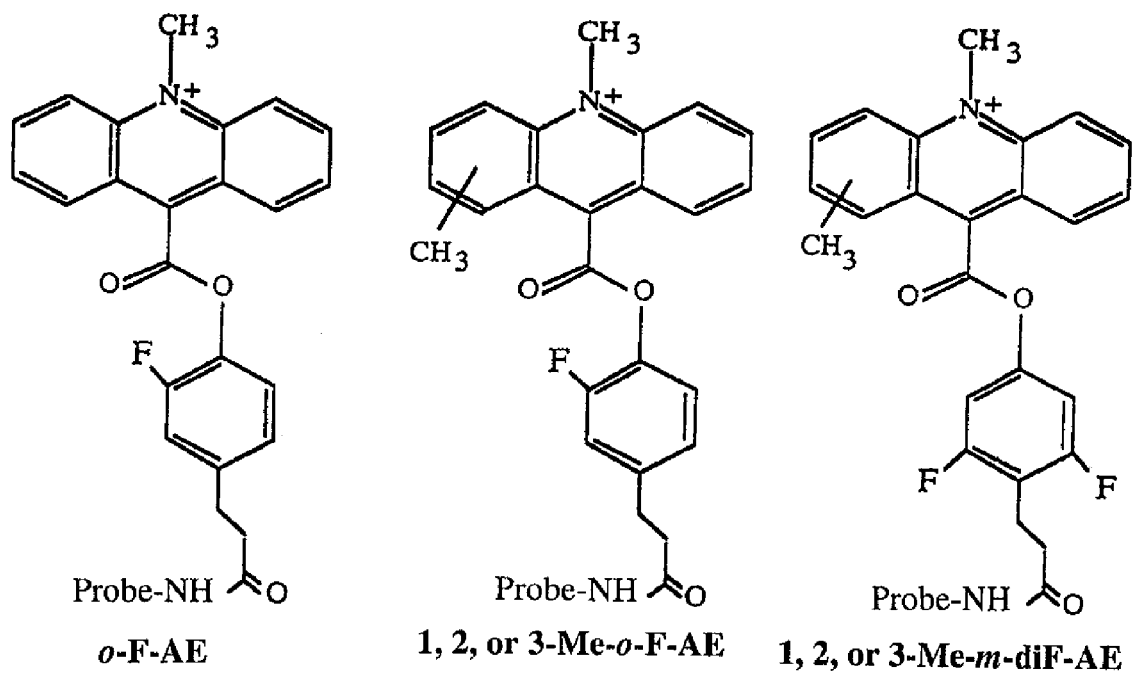

Unless clearly indicated otherwise, the following terms will have the indicated meanings throughout this specification.

By "nucleic acid analyte" or "analyte" is meant a nucleic acid sought to be detected in a sample or a nucleic acid synthesized as a result of a nucleic acid amplification reaction which contains at least about 20 nucleotides of the nucleotide base sequence of a nucleic acid sought to be detected in a sample or the complement thereof.

By "synthesizing" a nucleic acid or oligonucleotide is meant making the nucleic acid by chemical synthesis or enzymatic means. It is known that certain nucleic acid polymerase enzymes can incorporate modified nucleotides during enzymatic synthesis.

By "modified", a "modified nucleotide" or "modification" is meant a purposeful variant from the classical ribo- and deoxyribonucleotides A, T, G, C and U. When used in this specification, modified will mean a variant of the classical nucleotides, said variants leading to a higher binding efficiency when an oligonucleotide which contains said modified nucleotides is hybridized to a target nucleic acid than when the same oligonucleotide contains the classical nucleotides. In some cases an oligonucleotide having a modified 3' end may be referred to. This means that the 3' end of the oligonucleotide contains a substitution which inhibits or prevents extension of the 3' end by a nucleic acid polymerase.

By "conjugate molecule" is meant a molecule that can couple with an oligonucleotide in such a way that at least some of the characteristics of both the molecule and the oligonucleotide are retained in the combined product. Most often, the conjugate molecule contributes a new physical or chemical property to the oligonucleotide, while the oligonucleotide retains its ability to base pair.

By "binding affinity" is meant a measure of the strength of hydrogen bonding between at least partly complementary nucleic acids under defined nucleic acid hybridization conditions. A convenient measure of binding efficiency is the $T_m$, which is the temperature at which 50% of said two strands are in the double-stranded or hybridized form.

By "label" is meant a reporter moiety which is capable of being detected as an indication of the presence of the oligonucleotide to which it is joined. When the labeled oligonucleotide is hybridized to one or more other oligonucleotides, the presence of the label can be an indication of the presence of the other oligonucleotide or oligonucleotides as well. Appropriate reporter moieties are well known in the art and include, for example, radioisotopes, dyes, chemiluminescent, fluorescent, chemiluminescent and electrochemiluminescent compounds, nucleic acid sequences, enzymes, enzyme substrates, chromophores and haptens.

By "nucleic acid assay conditions" is meant environmental conditions, including temperature and salt concentration, for the preferential formation of stable hybrids between complementary base sequence regions over the formation of stable hybrids between non-complementary base sequence regions.

By "acridinium ester derivative" or "AE" is meant any of a family of chemiluminescent compounds derived from the acridinium ring which have a labelled ester or ester-like linkage at the C9 position connecting the acridinium ring to a leaving group. The leaving group is preferably an aryl or substituted aryl group. Substitutions, such as alkyl (e.g., methyl), alkoxy (e.g., methoxy), aryl and halide (e.g., Br and F), may be made to either or both the acridinium ring or the leaving group. Examples of such acridinium esters are provided in FIG. 1.

The methods and compositions of the present invention result from the unexpected discovery that oligonucleotides containing one or more nucleotides modified so that the oligonucleotides have an increased $T_m$ for a given target (as compared to otherwise identical unmodified oligonucleotides) will hybridize to a given target at an increased rate as compared to unmodified oligonucleotides. A maximum increase in the hybridization rate of a modified oligonucleotide occurs when a "cluster" of nucleotides are modified. By "cluster" is meant that at least about 4 of 5 consecutive nucleotides are so modified. Thus, oligonucleotides containing a mixture of modified and unmodified nucleotides may be just as effective in increasing target hybridization rate as in oligonucleotides containing 100% modified nucleotides. Aspects of the invention feature "chimeric" oligonucleotides containing both modified and unmodified nucleotides.

When used in this context, a "target" nucleic acid is a nucleic acid sought to be hybridized with an oligonucleotide. Such a nucleic acid may be a naturally occurring nucleic acid, e.g., ribosomal RNA, it may be the product (i.e., an "amplicon") of nucleic acid amplification methods such as PCR or a transcription-based amplification method, as described more fully below, or it may be another synthetic oligonucleotide.

Thus, the present invention is directed to diagnostic methods and compositions involving modified oligonucleotides which display an increase in the rate of oligo:target hybridization over an unmodified oligonucleotide of the same base sequence.

In a preferred embodiment, the invention utilizes modifications to the 2' position of the deoxyribofuranosyl (or ribofuranosyl) ring. The 2'-modification involves the placement of a group other than hydrogen or hydroxyl at the 2' position of the ribofuranosyl ring. Regardless of the nature of the substitution, it must not sterically hinder the ability of an oligonucleotide containing one or more such nucleotide modifications to hybridize to a single-stranded oligonucleotide having a complementary nucleotide base sequence. The hybridization of complementary, double-stranded nucleic acids in which one strand contains such modifications is markedly increased as compared to situations in which neither strand is so modified.

When a modified oligonucleotide is referred to as having an "increased" or "greater" affinity or rate, it is meant that the rate of hybridization or affinity of the modified oligonucleotide is greater than the hybridization rate or binding affinity of an unmodified oligonucleotide of the same length and base sequence to the same target.

Particularly preferred oligonucleotides are substituted with a methoxy group at the 2' sugar position. These 2'-modified oligonucleotides display a preference for RNA over DNA targets having a sequence identical to the RNA target (but having T substituted for U), with respect to both $T_m$ and hybridization kinetics. Other such oligonucleotides are known in the art.

Conjugate molecules attached to oligonucleotides modified as described herein may function to further increase the binding affinity and hybridization rate of these oligonucleotides to a target. Such conjugate molecules may include, by way of example, cationic amines, intercalating dyes, antibiotics, proteins, peptide fragments, and metal ion complexes. Common cationic amines include, for example, spermine and spermidine, i.e., polyamines. Intercalating dyes known in the art include, for example, ethidium bromide, acridines and proflavine. Antibiotics which can bind to nucleic acids include, for example, actinomycin and netropsin. Proteins capable of binding to nucleic acids include, for example, restriction enzymes, transcription factors, and DNA and RNA modifying enzymes. Peptide fragments capable of binding to nucleic acids may contain, for example, a SPKK (serine-proline-lysine (arginine)-lysine (arginine)) motif, a KH motif or a RGG (arginine-glycine-glycine) box motif. See, e.g., Suzuki, *EMBO J.*, 8:797-804 (1989); and Bund et al., *Science*, 265:615-621 (1994). Metal ion complexes which bind nucleic acids include, for example, cobalt hexamine and 1,10-phenanthroline-copper. Oligonucleotides represent yet another kind of conjugate molecule when, for example, the resulting hybrid includes three or more nucleic acids. An example of such a hybrid would be a triplex comprised of a target nucleic acid, an oligonucleotide probe hybridized to the target, and an oligonucleotide conjugate molecule hybridized to the probe. Conjugate molecules may bind to oligonucleotides by a variety of means, including, but not limited to, intercalation, groove interaction, electrostatic binding, and hydrogen bonding. Those skilled in the art will appreciate other conjugate molecules that can be attached to the modified oligonucleotides of the present invention. See, e.g., Goodchild, *Bioconjugate Chemistry*, 1(3):165-187 (1990). Moreover, a conjugate molecule can be bound or joined to a nucleotide or nucleotides either before or after synthesis of the oligonucleotide containing the nucleotide or nucleotides.

Applicant has also unexpectedly discovered that the observed increase in hybridization rate of modified oligonucleotides to their targets does not always increase indefinitely with an increasing number of contiguous modified nucleotides, especially when the target possesses an open or unfolded structure, or when helper probes are present. Under such circumstances, placement of modified nucleotides in a substantially contiguously arrangement, i.e., about 4 of 5 contiguous nucleotides, in the oligonucleotide, followed by hybridization to a complementary target, will result in an increased hybridization rate only up to a given number of modifications. The addition of modified nucleotides to the cluster past this number will not, in general, substantially further increase the hybridization rate.

In a currently preferred modification, employing 2'-O-methyl-substituted nucleotides, optimal hybridization rates are obtained in oligonucleotides having a cluster of about 8 contiguous modified residues. Given the discovery that modified oligonucleotides can increase the hybridization rate, it was unexpected that this effect does not always parallel the increase in $T_m$ contributed by such additions. That is, addition of modified oligonucleotides past the rate-optimal cluster size will continue to increase the $T_m$.

Although Applicant does not wish to be limited by theory, it is believed that such clusters function as "nucleation centers" which are the first regions of the oligonucleotide or nucleic acid to hydrogen-bond, in a rate-limiting step, followed by rapid hydrogen bonding of the remaining bases. While the entire oligonucleotide or nucleic acid may be so modified, little advantage in increased hybridization rate appears to be gained by substantially exceeding the optimal cluster size.

However, when the structure of the target is closed or folded in nature, and no helper probes are included, the hybridization rate between the oligonucleotide and the target generally may be improved by adding modified nucleotides to the oligonucleotide in excess of about 4 contiguous nucleotides. In a preferred embodiment, substantially all of the nucleotides of an oligonucleotide complementary to the structurally closed target will be modified.

The rate of in-solution hybridization of two complementary single-stranded nucleic acids depends on various factors, such as the concentration of the nucleic acids, the temperature of hybridization, and the properties of the solvent solution, such as salt concentration. Various methodologies have been employed to increase hybridization rates, the majority of which involve either changing the solvent system, such as by forming emulsions of immiscible solvents; by employing nucleic acid precipitating agents (e.g., Kohne et al., U.S. Pat. No. 5,132,207), or volume excusion agents, such as polyethylene glycol; or by increasing the concentration of a nucleic acid strand.

A problem associated with the latter approach in a diagnostic assay is that the target nucleic acid is usually present in quite small amounts. Thus, to increase the nucleic acid concentration necessitates using an excess of the oligonucleotide, resulting in increased cost and reagent waste and, if the oligonucleotide is labeled, risking unacceptably high backgrounds. The other methods, such as those requiring the use of multiple solvents and agents, such as polyethylene glycol, may present practical difficulties, such as excessive sample manipulation and time.

Therefore, one aspect of the present invention provides a means for increasing hybridization rates, as well as binding affinity, of oligonucleotides for RNA targets by using oligonucleotides containing nucleotides having a substitution at the 2' position of the ribofuranosyl ring ("2'-modified oligonucleotide"); preferably an alkoxy substitution, most preferably a methoxy substitution. These properties render useful methods employing such oligonucleotides in a diagnostic hybridization assay format by increasing the rate and extent of hybridization of such an oligonucleotide without requiring a concomitant increase in the concentrations of the hybridizing nucleic acids, a change in the properties or composition of the hybridization solution, the addition of "helper oligonucleotides", which are disclosed by Hogan et al., U.S. Pat. No. 5,030,557, the contents of which are hereby incorporated by reference herein, or an increase in the hybridization temperature. Nonetheless, the methods of the present invention may be used as supplements to one or more of these other techniques in any procedure in which an increase in the rate of nucleic acid hybridization would be advantageous.

As mentioned above, an advantage of this aspect of the invention relates to the ability of 2'-O-methyl modified oligonucleotides to preferentially hybridize to RNA over DNA, This property allows the design of oligonucleotide probes targeted to RNA. Probes can be made which would not tend to bind to DNA under stringent hybridization conditions, even where the DNA sequence is identical to the RNA target sequence (except that T is substituted for U in the DNA sequence). Such properties can be used in a number of different formats in which the specific detection of RNA would be advantageous. For example, to indicate and measure changes in the rate of transcription of particular RNA species, such as, for example, specific mRNA species, to monitor the effectiveness of a given therapy, to specifically probe tRNA or rRNA in preference to the genes encoding these RNA species, and to specifically detect RNA viruses in nucleic acid preparations containing large amounts of chromosomal DNA, even DNA preparations containing DNA versions of the viral sequences.

An additional advantage of this and other aspects is an increased target:oligo $T_m$ when using modified oligonucleotides, such as 2'-modified nucleotides as compared to the $T_m$ of target:oligo hybrids in which the oligonucleotide is a deoxyoligonucleotide. By "target:oligo" is meant a hydrogen bonded, double-stranded nucleic acid complex comprising a single-stranded oligonucleotide. The stability of the target:probe complex increases with an increase in the number of 2'-modified nucleotide residues contained in the probe. By contrast, the increase in the hybridization rate appears to be optimal in nucleic acids having a cluster of about 8 2'-modified nucleotide residues and does not increase significantly upon the addition of consecutive modified oligonucleotide residues above that number. Further, "chimeric" oligonucleotides having at least one such cluster of modified nucleotides could be designed to have greater hybridization rates without necessarily significantly increasing the $T_m$ of the oligonucleotide as a whole to its target.

An increased $T_m$ may be exploited in any diagnostic procedure in which the added stability of a nucleic acid duplex is desired. For example, higher hybridization temperatures can be used to accelerate the hybridization rate. A higher $T_m$ also permits the use of substantially shorter oligonucleotides than were heretofore practical, thus resulting in a savings in the costs associated with producing oligonucleotides for hybridization, as well as other advantages, as mentioned above.

In other aspects and embodiments of the present invention, chimeric oligonucleotides may contain a modified portion designed to bind to target nucleic acid and may also contain a deoxynucleotide portion which is either directly or indirectly able to bind to a solid phase-bound oligonucleotide. By way of example, and not of limitation, such an oligonucleotide may be a target capture oligonucleotide designed to bind a target nucleic acid (e.g., in solution) and link the bound target nucleic acid to a derivatized solid phase matrix, such as a bead, microsphere, polymeric substance, such as agarose or dextran or to a magnetized particle. Derivatives linked to such a matrix may include antibodies, ligands, or wholly or partially single-stranded oligonucleotides having a specific nucleotide sequence, such as a homopolymeric tract, designed to bind the capture oligonucleotide or an intermediate oligonucleotide. The bound target can then be further hybridized with a probe (either RNA, DNA or modified) and the unbound probe washed free of the immobilized target:probe complex before detecting the presence of the target nucleic acid.

It may be advantageous in certain instances to raise the temperature for hybridizing a modified oligonucleotide to its target. As described above, increasing the hybridization temperature also increases the rate of hybridization, so long as the hybridization temperature is sufficiently below the $T_m$ of the desired hybrid. The hybridization methods claimed herein, employing modified oligonucleotides having a higher $T_m$ than their unmodified counterparts, can be conducted at higher temperatures than would otherwise be used. In such a case, the rate increase associated with the modification alone is further increased by the raised temperature.

What follows are examples of embodiments of the invention, which should not be understood as limiting the scope of the invention thereto. Those skilled in the art will easily comprehend additional embodiments based on the disclosure contained in this specification. Additional embodiments are also contained within the claims which conclude this specification.

Modified Nucleic Acid Hybridization Assay Probes

Nucleic acid hybridization assays utilize one or more nucleic acid probes targeted to, i.e., having a nucleotide base sequence substantially complementary to, a nucleic acid sought to be detected. Often the probe will comprise an oligonucleotide (a single-stranded nucleic acid of between about 10 and about 100 nucleotides in length) which is synthetically made to have a given nucleotide sequence. By "substantially complementary" is meant that the oligo will bind to its target under appropriately selective conditions to form a hydrogen bonded duplex.

While a hybridization assay probe will generally be joined to a detectable label, the probe can be unlabeled and probe:target hybrids detected by, for example, UV absorbance, HPLC chromatography, gel electrophoresis and subsequent staining of the nucleic acid hybrid or other methods well known in the art. In hybridization assays, the probe and target are contacted with each other under conditions permitting stable and specific hybridization. The resulting hybrid is then separated from unlabeled hybrid and the label detected, or the label can be detected under conditions allowing the detection of the hybrid in preference to the unlabeled probe.

Methods for separating nucleic acids, such as gel exclusion chromatography, reverse phase chromatography, and hydroxyapatite adsorption, are known in the art. Applicant prefers an assay format wherein labeled hybrid and labeled unhybridized probe can be chemically differentiated by virtue of the formation of a double helix. A particularly preferred assay format is the hybridization protection assay (HPA), in which labeled unhybridized probe can be selectively be made undetectable while hybridized probe is relatively unaffected. See Arnold et al., U.S. Pat. No. 5,283,174. Thus, detection of label in this format is an indication of the labeled hybrid.

In these aspects, the present invention involves the use of modified oligonucleotides as probes in a hybridization assay. In one embodiment, modified oligonucleotides having a higher target-specific $T_m$ than unmodified oligonucleotides of the same base sequence are used to increase the rate of hybridization of the assay, as compared to assays employing unmodified oligonucleotides of the same base sequence. Such assay methods are able to utilize higher hybridization temperatures than are practicable using unmodified oligonucleotides. The higher hybridization temperature further increases the rate of hybridization and can also reduce the amount of cross-hybridization (hybridization of the probe with non-target sequences), thereby increasing the specificity of the assay.

The probes of this invention may comprise a cluster of about 4 or more substantially contiguous, modified nucleotide residues mixed with unmodified residues. Alternatively, the probe may comprise 100% modified residues. In preferred embodiments, the modifications are 2' substitutions, such as alkyl, alkoxy and halide substitutions to the 2' carbon of the ribofuranosyl nucleotide moiety. In particularly preferred embodiments, the substitution is a methoxy group.

Particular probe modifications, including 2'-O-methyl substitutions, result in the oligonucleotide having an increased affinity and increased hybridization rate to RNA targets but little effect on DNA affinity or rate of formation of probe:DNA hybrids. Again, this preference to RNA has been found to be optimized when the oligonucleotide has at least one cluster of from about 4 to about 8 modified bases.

Because oligonucleotides modified as described herein have a dramatically increased rate of hybridization, such modified oligonucleotide probes may be used in many cases without the need for the addition of unlabeled "helper probes", which are disclosed in Hogan, supra, as a means for increasing hybridization rates of probe to target. Nevertheless, Applicant has found that in some cases the combined use of such modified oligonucleotides and helper probes may operate in concert to increase the hybridization rate even further. In either case, the use of such modified oligonucleotides in diagnostic methods leads to more rapid identification of biological analytes, which in turn leads to, for example, to more effective treatments for disease conditions caused by or indicated by such analytes.

As described in more detail below, Applicant has found that probes displaying a preferential affinity to RNA targets may be used to specifically detect RNA over DNA of the same sequence (except that U is substituted for T in the RNA sequence). Such methods have application in, for example, the specific detection of RNA viruses in cells containing DNA versions of the viral genome, or in specific detection of levels of RNA transcription in cells.

Probes may also be devised which contain both target-complementary sequences as well as additional target, non-complementary sequences. These target, non-complementary sequences may have other functions. For example, the sequences may be complementary to another oligonucleotide or target nucleic acid, or they may have functional properties, such as promoter sequences and restriction sites. Thus, a probe may have more than one function, only one of which is to be detected as an indication of the presence of a target.

Additionally, probes may be designed to have at least one nucleic acid strand which has at least two separate target-complementary sequences that can hybridize to a target nucleic acid. An example of such probes is described by Hogan et al., U.S. Pat. Nos. 5,424,413 and 5,451,503, which are incorporated by reference herein. The probes disclosed by Hogan et al. further include at least two distinct arm regions that do not hybridize with the target, but possess complementary regions that are capable of hybridizing with one another. These arm regions can be designed to require the presence of target in order for their complementary sequences to hybridize under suitable hybridization conditions. Accordingly, target-complementary sequences of the probe must hybridize to the target before complementary arm regions can hybridize to each other. The resulting structure is termed a branched nucleic acid.

Figure 2:
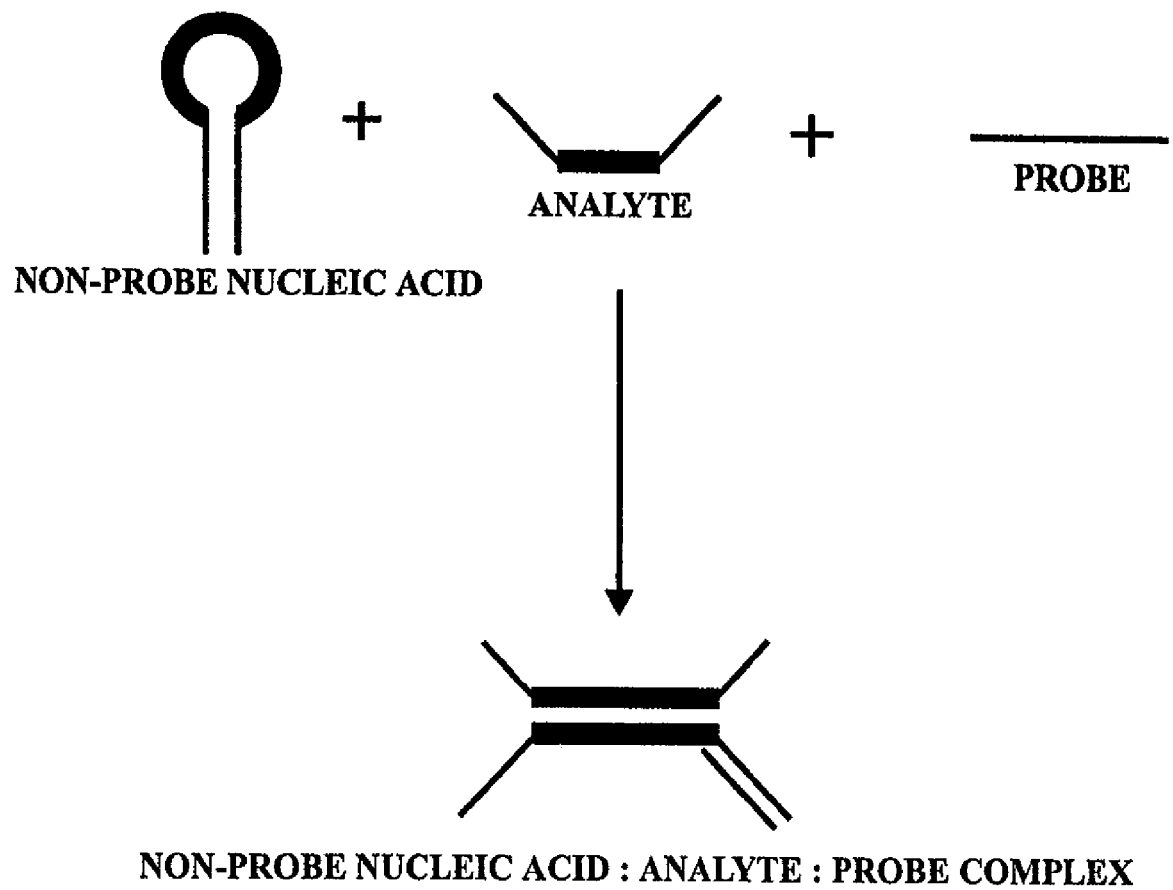
FIG. 2 shows an arrangement whereby detection of an analyte first requires the hybridization of the analyte to a nucleic acid other than the probe. According to this arrangement, the probe is unable to bind with either the analyte or the non-probe nucleic acid before the analyte has hybridized to the non-probe nucleic acid. (Bolded portions represent regions of complementary between the analyte and the non-probe nucleic acid.) However, hybridization of the analyte to the non-probe nucleic acid alters the configuration of the non-probe nucleic acid sufficiently to enable hybridization of the non-probe nucleic acid to the probe, thus permitting detection of the analyte.

Other probes may be designed which are unable to specifically bind the target. To be useful in detecting target, these probes must be able to hybridize with another nucleic acid that can bind with the target, either directly or indirectly. In one such arrangement, a nucleic acid can be structured to contain at least a first and second, nonoverlapping nucleotide base sequence regions, where the first nucleotide region is complementary to a nucleotide base sequence of the target and the second nucleotide region is complementary to a nucleotide base sequence of the probe. In this arrangement, the second nucleotide region of the nucleic acid would be unavailable for binding with the probe until the target has hybridized with the first nucleotide region of the nucleic acid. Binding of the nucleic acid and target would alter the configuration of the nucleic acid, thus permitting the second nucleotide region of the nucleic acid to bind with the probe. See FIG. 2. Of course, this arrangement could be modified so that indirect binding between the nucleic acid and target, accomplished with one or more intervening or coupling nucleic acids, would render the second nucleotide region of the nucleic acid available for binding with the probe.

Modified Nucleic Acid Amplification Oligonucleotides

In still other aspects, the present invention includes methods for employing modified oligonucleotide primers, promoter-primers, and/or splice templates for nucleic acid amplification and compositions comprising such oligonucleotides, wherein the oligonucleotides contain at least one cluster of modified bases which cause an increased rate of hybridization.

Primer-employing amplification methods include the polymerase chain reaction method (PCR) and its variations, as described by Mullis, et al., (see U.S. Pat. Nos. 4,683,195, 4,683,202, and 4,800,159, European Patent Application Nos. 86302298.4, 86302299.2, and 87300203.4, and 155 *Methods in Enzymology*, 335-350 (1987)). The PCR methodology is by now a matter of common knowledge to those skilled in the art.

PCR has been coupled to RNA transcription by incorporating a promoter sequence into one of the primers used in the PCR reaction and then, after amplification by the PCR method, using the double-stranded DNA as a template for the transcription of single-stranded RNA. (See, e.g., Murakawa et al., *DNA*, 7:287-295 (1988)).

Other amplification methods use multiple cycles of RNA-directed DNA synthesis and transcription to amplify DNA or RNA targets. See, e.g., Burg et al., U.S. Pat. No. 5,437,990; International Publication No. WO 89/1050; Gingeras et al., International Publication No. WO 88/10315; Davey et al., European Publication No. 0 329 822; Malek et al., International Publication No. WO 91/02818, Kacian et al., U.S. Pat. No. 5,480,783; McDonough et al., International Publication No. WO 94/03472; and Kacian et al., International Publication No. WO 93/22461 (each of these references is incorporated by reference herein). Urdea et al., International Publication No. WO 91/10746, describe a method that achieves signal amplification using a T7 promoter sequence.

Each of these methods makes use of one or more oligonucleotide primers or splice templates able to hybridize to or near a given nucleotide sequence of interest. After hybridization of the primer, the target-complementary nucleic acid strand is enzymatically synthesized, either by extension of the 3' end of the primer or by transcription, using a promoter-primer or a splice template. In some amplification methods, such as PCR, rounds of primer extension by a nucleic acid polymerizing enzyme is alternated with thermal denaturation of complementary nucleic acid strands. Other methods, such as those of Kacian et al., U.S. Pat. No. 5,480,783 and International Publication No. WO 93/22461, and McDonough et al., International Publication No. WO 94/03472, are isothermal transcription-based amplification methods.

In each amplification method, however, side reactions caused by hybridization of the primer to non-target sequences can reduce the sensitivity of the target-specific reaction. These competing "mismatches" may be reduced by raising the temperature of the reaction. However, raising the temperature may also lower the amount of target-specific primer binding as well.

Thus, according to this aspect of the invention, primers having high target affinity, and comprising modified nucleotides in the target binding region, may be used in nucleic acid amplification methods to more sensitively detect and amplify small amounts of a target nucleic acid sequence, by virtue of the increased temperature, and thus the increased rate of hybridization to target molecules, while reducing the degree of competing side-reactions (cross-reactivity) due to non-specific primer binding. Preferred oligonucleotides contain at least one cluster of modified bases, but less than all nucleotides are modified in preferred oligonucleotides.

In another preferred embodiment, modified oligonucleotide primers are used in a nucleic acid amplification reaction in which a target nucleic acid is RNA. See, e.g., Kacian et al., U.S. Pat. No. 5,480,783. The target may be the initially present nucleic acid in the sample, or may be an intermediate in the nucleic acid amplification reaction. In this embodiment the use of preferred 2'-modified primers, such as oligonucleotides containing 2'-O-methyl nucleotides, permits their use at a higher hybridization temperature due to the relatively higher $T_m$ conferred to the hybrid, as compared to the deoxyoligonucleotide of the same sequence. Also, due to the preference of such 2'-modified oligonucleotides for RNA over DNA, competition for primer molecules by non-target DNA sequences in a test sample may also be reduced. Further, in applications wherein specific RNA sequences are sought to be detected amid a population of DNA molecules having the same (assuming U and T to be equivalent) nucleic acid sequence, the use of modified oligonucleotide primers having kinetic and equilibrium preferences for RNA permits the specific amplification of RNA over DNA in a sample.

Sample Processing

In accord with the present invention, modified oligonucleotides having increased target-specific hybridization kinetics and binding affinities as compared to their unmodified analogues may be used in a variety of hybridization assay sample processing methodologies.

By sample processing is meant methods allowing or enhancing the discrimination of analyte and non-analyte nucleic acids. Such methods may involve, for example, the direct or indirect immobilization of nucleic acids or oligonucleotides from the liquid phase in a heterogeneous assay. Some such methods may involve two or more hybridization events resulting in such immobilization.

For example, Ranki et al., U.S. Pat. Nos. 4,486,539 and 4,563,419, discuss a one-step nucleic acid "sandwich" hybridization method involving the use of a solid-phase bound nucleic acid having a target complementary sequence and a labeled nucleic acid probe, complementary to a separate portion of the target nucleic acid. Stabinsky, U.S. Pat. No. 4,751,177, discusses methods involving the use of a "mediator" polynucleotide which reportedly overcomes sensitivity problems in the Ranki method associated with leakage of the immobilized oligonucleotide from the solid support.

Other methods may employ an immobilized oligonucleotide, for example an oligonucleotide containing a homopolymeric tract, such as poly T, or a simple short repeating sequence, and two or more coupling oligonucleotides, one of which is able to hybridize with the immobilized oligonucleotide and a different one of which is able to specifically hybridize with target. Each of the coupling oligonucleotides is able to bind at least one other coupling oligonucleotide. If a coupling oligonucleotide does not contain a sequence complementary to the target or immobilized oligonucleotide, it will be able to hybridize with at least two other coupling oligonucleotides simultaneously. The solid support may be comprised of materials including nitrocellulose, a polymeric substance, such as polyacrylamide or dextran, metallic substances or controlled pore glass. The support may be in forms such as a sheet, membrane or a particle. Additionally, the solid support may have a magnetic charge to facilitate recovering sample and/or washing away unbound nucleic acids or other sample components.

Joining of the immobilized oligonucleotide to the solid support may be accomplished by any method that will continue to bind the immobilized oligonucleotide throughout the assay steps. Additionally, it is important that when the solid support is to be used in an assay, it be essentially incapable, under assay conditions, of the non-specific binding or adsorption of non-target oligonucleotides or nucleic acids.

Common immobilization methods include binding the nucleic acid or oligonucleotide to nitrocellulose, derivatized cellulose or nylon and similar materials. The latter two of these materials form covalent interactions with the immobilized oligonucleotide, while the former binds the oligo through hydrophobic interactions. When using these materials it is important to use a "blocking" solution, such as those containing a protein, such as bovine serum albumin (BSA), or "carrier" nucleic acid, such as salmon sperm DNA, to occupy remaining available binding sites on the solid support before use in the assay.

Other immobilization methods may include the use of a linker arm, for example, N-hydroxysuccinamide (NHS) and its derivatives, to join the oligonucleotide to the solid support. Common solid supports in such methods are, without limitation, silica, polyacrylamide derivatives and metallic substances. In such a method, one end of the linker may contain a reactive group (such as an amide group) which forms a covalent bond with the solid support, while the other end of the linker contains another reactive group which can bond with the oligonucleotide to be immobilized. In a particularly preferred embodiment, the oligonucleotide will form a bond with the linker at its 3' end. The linker is preferably substantially a straight-chain hydrocarbon which positions the immobilized oligonucleotide at some distance from the surface of the solid support. However, non-covalent linkages, such as chelation or antigen-antibody complexes, may be used to join the oligonucleotide to the solid support.

A desirable embodiment of the latter assay system contains two coupling oligonucleotides: (i) a first coupling oligonucleotide containing a nucleotide sequence substantially complementary to the immobilized oligonucleotide, for example, with a poly A nucleotide sequence complementary to a poly T sequence on the immobilized oligo, and (ii) a second coupling oligonucleotide containing a nucleotide sequence substantially complementary to the target nucleic acid, a detectably labeled probe, or both. In a preferred embodiment, the second coupling oligonucleotide contains a nucleotide sequence substantially complementary to the target nucleic acid. Moreover, each coupling oligonucleotide in the preferred embodiment contains another nucleotide sequence which enables the first and second coupling oligonucleotides to hybridize to each other under assay conditions. However, one or more additional coupling oligonucleotides may be introduced into the system, such that the first and second coupling oligonucleotides are indirectly bound to each other by means of these additional, intervening coupling oligonucleotides. The additional coupling oligonucleotides would be substantially unable to hybridize with the any of the target nucleic acid, the detectably labeled oligonucleotide probe, or the immobilized oligonucleotide under assay conditions.

Yet another assay system having practical advantages in ease and rapidity of use may comprise an immobilized oligonucleotide having a portion complementary to a capturing oligonucleotide. The capturing oligonucleotide (capture probe) will contain a base sequence permitting hybridization to the target. The capturing oligonucleotide will also have a label attached within or near the target-binding nucleotide sequence region, such as a substituted or unsubstituted acridinium ester, which may be used in a homogeneous or semi-homogenous assay system to specifically detect hybrid nucleic acids without detecting single-stranded nucleic acids, such as the capture probe itself. Such a system favored by Applicant is the HPA, which is discussed and incorporated by reference above. In the HPA format, the label contained on any capture probe which has not hybridized to its target will be hydrolyzed with the addition of base, while target:capture probe hybrid would protect the label associated therewith from hydrolysis.

An advantage to this latter assay system is that only one target-specific hybridization event (labeled capture probe: target) need occur for target detection, rather than two such events (capture probe:target and labeled probe:target) in the other sample processing procedures described herein. Fewer oligonucleotides in the assay would tend to make the assay faster and simpler to optimize, since the overall rate at which labeled target is captured is limited by the slowest hybridizing probe. Additionally, while the portion of the target complementary to the capturing oligonucleotide in these other assay systems does not have to be as specific as the target's probe binding region, this base sequence must be rare enough to avoid significant saturation of the capture probe with non-target nucleic acids. Thus, this preference for two separate and specific target sequences may place constraints on finding an appropriate target to which such assays are to be directed. By contrast, only one such target sequence need be found in the latter assay, since the same nucleotide sequence functions simultaneously to immobilize and detect the target nucleic acid.

Regardless of the approach used, a necessary element of any assay is a method of detection of the desired target. A number of options known to those of skill in the art are possible. One such option is the direct use of a labeled nucleic acid probe. Such a probe would have a nucleotide sequence region which is specifically hybridizable with and substantially complementary to the target nucleic acid of interest. Upon hybridization to the target and immobilization of the target:probe hybrid, unbound probe can be washed away or inactivated and the remaining label hybrid-associated detected and/or measured.

Another option combines the elements of detection and nucleic acid amplification. In such a system, the target nucleic acid is immobilized as described, for example, and without limitation, in the assay procedures described above. One or more amplification oligonucleotides (see, e.g., Kacian et al., International Publication No. WO 93/22461), such as a primer, promoter-primer, or splice template, able to hybridize with a specific region of the target nucleic acid may be contacted with the immobilized target nucleic acid under nucleic acid amplification conditions, for example, in the presence of one or more nucleic acid polymerases and ribo- and/or deoxyribonucleotide triphosphates.

The resulting polynucleotide strand (amplicon) can be made directly available for specific hybridization and detection with a labeled hybridization assay probe or for further amplification by hybridizing the polynucleotide strand with one or more additional amplification oligonucleotides under nucleic acid amplification conditions. If the latter option is chosen, the amplification reaction can be continued until the desired level of amplification is achieved, then the resulting amplicons, which may comprise copies of at least a portion of the immobilized target nucleic acid, polynucleotides complementary to at least a portion of the immobilized nucleic acid, or both, can be detected using one or more labeled oligonucleotide probes. If the amplification reaction is to take place while the target is immobilized, it is important that the portion of the target molecule to be used as a template for the amplicons not contain the nucleotide sequence region necessary for immobilization of the target nucleic acid. Although amplicons of either or both senses can be detected with the labeled probes, in a preferred embodiment only amplicons of the opposite sense to, i.e., complementary to, the immobilized target are detected.

A heterogeneous target capture method such as this is particularly advantageous since crude clinical samples can contain substances which inhibit or interfere with the amplification reaction. Thus, the ability to separate the target nucleic acid from such interfering substances can permit or enhance the sensitivity of nucleic acid amplification.

This solid-phase associated amplification scheme can be used in myriad assay systems, including those described above. Applicant currently prefers an assay system employing one or more coupling oligonucleotides, as described above, which are able to indirectly link the target nucleic acid to the solid support. It is also preferred that the complementary nucleotide sequence regions of the support-coupled oligonucleotide, and the capturing oligonucleotide designed to hybridize to it, be at least partially homopolymeric or contain simple repeating nucleotide sequences, so as to promote rapid hybridization. Additionally, or alternatively, these regions of either or both the immobilized oligonucleotide and the capturing oligonucleotide may be modified in a manner consistent with the disclosure of this specification to increase the rate of hybridization between these oligonucleotides. In such a system, the target capture oligonucleotide and the target nucleic acids are preferably allowed to hybridize in solution before hybridizing to the immobilized oligonucleotide. In the currently preferred embodiment, the immobilized target is washed, the amplification oligonucleotide (or oligonucleotides) is contacted with the immobilized target under nucleic acid amplification conditions, and following amplification the labeled amplicon-directed probe is added and detected.

Applicant prefers to use the transcription-based amplification method described in Kacian et al., U.S. Pat. No. 5,480, 783. In accord with this method, a promoter-primer having a 3' region complementary to a portion of the target and a 5' region and a primer having the same nucleotide sequence as a portion of the target are contacted with a target RNA molecule. The primer and promoter-primer define the boundaries of the target region to be amplified, including both the sense present on the target molecule and its complement, and thus the length and sequence of the amplicon. In this preferred embodiment, the amplification oligonucleotides and immobilized target RNA are contacted in the presence of effective amounts of Moloney murine leukemia virus-derived reverse transcriptase and T7 RNA polymerase, both ribonucleotide and deoxyribonucleotide triphosphates, and necessary salts and cofactors at 42° C. Under these conditions, nucleic acid amplification occurs, resulting predominantly in production of RNA amplicons of a sense opposite to that of the target nucleic acid. These amplicons are then detected, e.g., by using an acridinium ester-labeled hybridization assay probe of the same sense as the target-nucleic acid, in the hybridization protection assay disclosed in Arnold, supra, previously incorporated by reference.

In this preferred embodiment, Applicant prefers that the 3' terminus of the immobilized oligonucleotide, target capture oligonucleotide and coupling oligonucleotide(s) be "capped" or blocked to prevent or inhibit their use as templates for nucleic acid polymerase activity. Capping may involve addition of 3'deoxyribonucleotides (such as cordycepin), 3',2'-dideoxynucleotide residues, non-nucleotide linkers, such as disclosed in Arnold, et al., supra, alkane-diol modifications, or non-complementary nucleotide residues at the 3' terminus.

Although Applicant currently prefers to contact the primers with the target following target immobilization, there may be hybridization kinetic advantages to combining the target nucleic acid and at least one primer complementary thereto at the same time that the target capture oligonucleotide is added. Applicant believes that it is advantageous to conduct the target hybridization in solution prior to immobilization of the target, as hybridization can take place in solution more rapidly than when one nucleic acid is immobilized.

Likewise, while Applicant prefers to form and detect amplicons of the opposite sense to the target, there is no reason why one could not form and detect amplicons of either or both senses. Additionally, when amplifying target nucleic acids contained in crude clinical samples, it appears important to conduct a wash step prior to the amplifying step to prevent enzyme inhibition and/or nucleic acid degradation due to substances present in the sample.

It will be clear to the skilled person that this methodology is amenable, either as described or with obvious modifications, to various other amplification schemes including the polymerase chain reaction.

Modified Oligonucleotides in Sample Processing

Modified oligonucleotides able to hybridize to complementary targets with increased kinetics may be used in sample processing methods which employ nucleic acid hybridization, including the target capture methods described above. In light of the present disclosure it will be apparent that such partly or wholly modified oligonucleotides may be employed as hybridization assay probes or amplification oligonucleotides in these systems. Additionally, wholly or partially modified oligonucleotides having increased target-directed hybridization kinetics may be used as immobilized oligonucleotides, target capture oligonucleotides, and/or one or more coupling oligonucleotides in heterogenous assays employing nucleic acid hybridization. For example, such modifications may be used to reduce the overall assay time or to allow the hybridization steps of the assay to occur at a single temperature. The advantages of reduced time and ease of assay operation in a clinical setting gained thereby would be clear to those skilled in the art.

Additionally, oligonucleotides may be modified to have hybridization kinetics and/or equilibrium preferences for a specific type of nucleic acid, such as RNA or DNA. As disclosed above, for example, 2'-O-methyl oligonucleotides preferentially hybridize with RNA over DNA. Thus, target capture oligonucleotides containing 2'-O-methyl nucleotides may be used to specifically capture RNA target nucleic acids, such as mRNA or rRNA, under hybridization conditions not promoting hybridization of the oligonucleotide to the genomic versions thereof. Likewise, 2'-O-methyl-modified amplification oligonucleotides and/or labeled probes can be designed, thereby targeting RNA over DNA for amplification and/or detection, as described above.

Modified Helper Oligonucleotides

Helper oligonucleotides are described in the Hogan, supra. Helper oligonucleotides are generally unlabeled and used in conjunction with labeled hybridization assay probes to increase the labeled probe's $T_m$ and hybridization rate by "opening up" target nucleotide sequence regions which may be involved in secondary structure, thus making these regions available for hybridization with the labeled probe.

In light of the present disclosure, those of skill in the art will easily recognize that using modified helper oligonucleotides which will hybridize with the target nucleic acid at an increased rate over their unmodified counterparts can lead to even greater hybridization rates of the labeled probe to their target. Thus, methods and compositions for detecting oligonucleotides employing such modified helper oligonucleotides are intended to be encompassed within the scope of this invention. Preferred helper oligonucleotides have modifications which give them a greater avidity towards RNA than DNA. In a preferred embodiment, such modifications include a cluster of at least about 4 2'-O-methyl nucleotides. In a particularly preferred embodiment, such modifications would include a cluster of about 8 2'-O-methyl nucleotides.

Diagnostic Kits

The methods described herein also clearly suggest diagnostic kits specially formulated for use in such methods. These kits will contain one or more oligonucleotides to be used in a diagnostic nucleic acid hybridization assay. At least one of these oligonucleotides will contain a cluster of at least about 4 modified nucleotides designed to hybridize to a target nucleic acid region at an increased rate over an otherwise identical oligonucleotide.

Such diagnostic kits may include, without limitation, one or any combination of the probe, amplification, helper and sample processing oligonucleotides described herein.

In a preferred embodiment of the present invention, the kit contains at least one labeled oligonucleotide probe having a region containing one or more clusters of at least about 4 contiguous 2'-modified nucleotide residues. In amore preferred embodiment, the region contains one or more clusters of about 8 2'-modified nucleotides.

Applicant currently prefers using an acridinium ester derivative as a non-radioactive label and the addition of a methoxy group as a 2' modification. In a particularly preferred embodiment, at least one of the modified oligonucleotides will comprise one or more clusters of at least about 4 2'-O-methyl nucleotides. Even more preferred is at least one oligonucleotide containing one or more clusters of about 8 2'-O methyl nucleotides.

Kits containing one or more of the modified oligonucleotides disclosed herein could be sold for use in any diagnostic hybridization assay method, or related amplification method, of the present invention. In such an assay, at least one of the modified oligonucleotides contained in the kit would function as a probe able to hybridize to a target nucleic acid. If the modified probe is contacted with a sample containing the target nucleic acid, the probe will exhibit improved hybridization properties over an unmodified probe having an identical base sequence. For instance, the hybridization binding affinity between the target and the probe will be greater than the hybridization binding affinity between the target and an unmodified form of the probe, when subjected to the same hybridization assay conditions. Additionally, the hybridization rate between the target and the probe will be greater than the hybridization rate between the target and an unmodified form of the probe, when subjected to the same hybridization assay conditions.

To further improve the hybridization properties of the probe, one or more conjugate molecules may be bound to the probe, preferably in a region containing a cluster of at least about 4 modified nucleotides. It is also expected that the kit would be packaged with instructions for using one or more modified oligonucleotides in a diagnostic hybridization assay of the present invention.

Objects

It is therefore an object of the present invention to provide methods for increasing the both the avidity of binding and the hybridization rate between a diagnostic nucleic acid probe and its target nucleic acid by utilizing probe molecules having one or more modified nucleotides, preferably a cluster of about 4 or more, and more preferably about 8, modified nucleotides. In preferred embodiments, the modifications comprise 2' modifications to the ribofuranosyl ring. In most preferred embodiments the modifications comprise a 2'-O-methyl substitution.

It is also an object to provide methods for increasing the rate of hybridization of a single-stranded oligonucleotide to a target nucleic acid through the incorporation of a plurality of modified nucleotides into the oligonucleotide. An increased rate of hybridization accomplished in this manner would occur over and above the increase in hybridization kinetics accomplished by raising the temperature, salt concentration and/or the concentration of the nucleic acid reactants.

It is another object of the invention to provide diagnostic methods for selectively targeting RNA over DNA through the use of oligonucleotides modified to have an increased target binding efficiency and to hybridize to RNA at an enhanced rate over DNA. In a preferred embodiment, such oligonucleotides comprise a 2'-O-methyl modification to the ribofuranosyl ring.

It is an additional object of the invention to provide sample processing methods which employ an immobilized oligonucleotide to directly or indirectly capture target nucleic acids. In preferred embodiments, such methods employ one or more oligonucleotides which can specifically hybridize to the target nucleic acid, permitting its detection and immobilization. In a preferred embodiment, a single labeled oligonucleotide is responsible for both capture and detection of the target. In a particularly preferred embodiment, a coupling or bridging nucleic acid is bound to both the immobilized oligonucleotide and the oligonucleotide responsible for capture and detection of the target. Additional coupling nucleic acids are possible. Some or all of the oligonucleotides used in sample processing methods may contain modifications which accelerate the rate of target specific hybridization.

It is yet another object of the invention to provide target specific oligonucleotides of between about 10 and about 100 bases, preferably between about 10 and about 15 bases, and more preferably between about 12 and about 15 bases, which preferably contain at least one cluster of at least about 4 nucleotides, more preferably about 8 nucleotides, modified to increase their target-specific binding efficiency while simultaneously increasing their discrimination between target and non-target nucleotide sequences as compared to longer unmodified oligonucleotides designed to hybridize to the same site.

It is a further object of the present invention to provide kits including one or more oligonucleotides containing modified nucleotides which function to increase the rate of hybridization between the oligonucleotide and a target nucleic acid. Kits of the present invention could include any combination of probe, amplification, helper and sample processing oligonucleotides. In a preferred embodiment, the modified oligonucleotides of these kits would contain at least one cluster of about 4 2'-O-methyl modifications to the ribofuranosyl ring. Kits containing these modified oligonucleotides may be supplied for use in both diagnostic hybridization assays and amplification assays. Such kits may further include written instructions directing practitioners in the use of the modified oligonucleotides in either or both diagnostic hybridization assays or amplification assays.

The diagnostic methods of the present invention are, therefore, specially adapted to exploit the hybridization properties of modified oligonucleotides having increased binding affinity. These methods may be used for the detection or quantification of any target nucleic acid. In a preferred embodiment, the target nucleic acid is RNA. The methods may employ "chimeric" oligonucleotides composed of regions of unmodified oligodeoxy- or oligoribonucleotides combined with regions of modified oligonucleotides or may utilize wholly modified oligonucleotides. Preferably, the oligonucleotides are not wholly modified. The regions may be designed simply to promote rapid hybridization of probe to target, or may have other functions. For example, a chimeric oligonucleotide may be designed to bind both to RNA and to DNA. In such a case, the RNA-binding portion of the oligonucleotide may contain a plurality of modified nucleotides to preferentially bind the RNA target. Alternatively, the region of modified residues may be designed to be directed towards a target present in low abundance in order to increase the hybridization rate.

Given the present disclosure, it will be understood that certain embodiments of the methods and compositions, including the kits, of the present invention may employ oligonucleotides having more than one type of modification affecting the hybridization properties of the resulting oligonucleotide, i.e., $T_m$ and hybridization kinetics. Such multiple modifications may act in a cooperative fashion to further increase the hybridization rate or to increase the specificity of the resulting oligonucleotide for a given type of nucleic acid target, such as RNA. Furthermore, chimeric oligonucleotides may have or consist of regions of differently modified oligonucleotides containing either 2'-modified nucleotides or nucleotides having other modifications or both.

The objects and aspects of the invention specifically described herein are not intended as an exhaustive listing of the objects or aspects of the methods and compositions of the present invention which would be apparent to those skilled in the art in light of the present disclosure. Nor should the preceding description or the Examples which follow be construed as limiting the invention to the embodiments specifically disclosed therein.

EXAMPLES

Unless otherwise indicated, in all the following examples oligodeoxyribonucleotides, oligoribonucleotides, and modified oligonucleotides were synthesized by use of standard phosphoroamidite chemistry, various methods of which are well known in the art. See, e.g., Carruthers et al., 154 *Methods in Enzymology*, 287 (1987), which is hereby incorporated by reference as part of this disclosure. Unless otherwise stated herein, modified nucleotides were 2' O-methyl-nucleotides, which were used in the synthesis as their phosphoramidite analogs. Applicant prepared the oligonucleotides using an Expedite 8909 DNA Synthesizer (PerSeptive Biosystems, Framingham, Mass.).

Also, unless otherwise indicated, oligonucleotides indicated as labeled contained an acridinium phenyl ester. Acridinium phenyl ester compounds are derivatives of acridine possessing a quaternary nitrogen center and derivatized at the 9 position to yield a phenyl ester moiety. However, leaving groups other than phenyl moieties are well known in the art. Acridinium esters have the property of reacting with hydrogen peroxide to form a transient dioxetane ring involving the C-9 carbon of the acridinium ring, followed by the formation of an excited acridone. The radiative relaxation of the excited acridone results in the production of light. The synthesis of acridinium esters, as well as a general description of their use as chemiluminescent labeling reagents, is described in Weeks et al., *Acridinium Esters as High Specific Activity Labels in Immunoassays, Clin. Chem.*, 29:1474-1478 (1984), which is incorporated by reference herein.

In these Examples, the acridinium esters were attached, using standard chemical techniques, to a non-nucleotide monomeric unit having a primary amine "linker arm" joined to the acridinium ester moiety, which is inserted between contiguous sequences of nucleotides during the chemical synthesis of the oligonucleotides, or placed at a terminal position of the oligonucleotide. See, Arnold et al., "Non-Nucleotide Linking Reagents for Nucleotide Probes," European Publication No. 0 313 219, which is incorporated by reference herein. However, it will be understood that the preference of 2'-modified oligonucleotides for RNA targets and the effect of the modified oligonucleotides on the rate of hybridization to DNA targets are not determined by the presence or specific nature of a label. Thus, those of skill in the art will recognize that oligonucleotides used in the methods of the present invention may be labeled with a variety of labels, or they may be unlabelled when, for example, they are used as amplification primers, helper oligonucleotides or in a capture assay.

Acridinium ester derivatives may be joined to the linker arm:hybridization probe conjugate using techniques well known in the art. Preferably, Applicant uses the methods described in Nelson et al., *Detection of Acridinium Esters by Chemiluminescence in Non-Isotopic Probe Techniques* (Academic Press 1992), and Arnold et al., European Publication No. 0 313 219.

Further, unless expressly indicated otherwise, all target nucleic acids were RNA.

It will nevertheless be clear to those of skill in the art, in light of the present disclosure, that other labels may be used in the methods and compositions of the present invention without departing from the spirit of the invention disclosed herein.

Example 1

Effect of 2' Modifications on the $T_m$ of Probe:Target Hybrids

Oligonucleotide probes of identical sequence containing varying amounts of 2'-O-methyl nucleotides were each individually hybridized to perfectly complementary synthetic RNA targets of the same length. The target sequence (SEQ ID NO: 1) and the probe sequences (SEQ ID NO:2-6) were as follows (reading 5' to 3'):

SEQ ID NO:1:  atgttgggttaagtcccgcaacgagc;

SEQ ID NO:2:  gctcgttgcgggacttaacccaacat (Probe A);

-continued

SEQ ID NO:3:  gcucguugcgggacuuaacccaacau (Probe B);

SEQ ID NO:4:  gcucguugcgggacttaacccaacau (Probe C);

SEQ ID NO:5:  gctcgttgcgggacuuaacccaacat (Probe D); and

SEQ ID NO:6:  gctcgttgcgggacuuaacccaacat (Probe E).

These probes were synthesized to contain no 2'-O-methyl nucleotides (Probe A), all 2'-O-methyl nucleotides (Probe B), or a combination of deoxy- and 2'-O-methyl nucleotides (Probes C, D and E), and each probe was labeled with an acridinium phenyl ester compound joined to a linker arm attached to the probe between nucleotides 16 and 17 (reading 5' to 3'). The bolded nucleotides represent 2'-O-methyl nucleotides. Probe C contained four contiguous deoxyribonucleotides positioned directly adjacent to each side of the linker attachment site and 2'-O-methyl ribonucleotides at all other bases; Probe D contained four contiguous 2'-O-methyl nucleotides positioned directly adjacent to each side of the linker attachment site and deoxyribonucleotides at all other bases, and Probe E contained eight contiguous 2'-O-methyl nucleotides positioned directly adjacent to each side of the linker attachment site and deoxyribonucleotides at all other bases. The $T_m$ of each hybrid was determined using both a chemiluminescent and an optical method.

Chemiluminescent Method

Using the chemiluminescent method, approximately 1 μmol of the RNA target and 0.1 μmol of each oligonucleotide probe, labeled as described above with "standard" acridinium ester (4-(2-succinimidyloxycarbonyl ethyl) phenyl-10-methylacridinium 9-carboxylate fluorosulfonate) were allowed to hybridize at 60° C. for 60 minutes in 30 μl of lithium succinate buffer (1.5 mM EDTA (ethylenediaminetetraacetic acid), 1.5 mM EGTA (ethylene glycol-bis(β-aminoethyl ether) N,N,N',N'-tetraacetic acid), 310 mM lithium lauryl sulfate, 0.1 M lithium succinate (pH 5.2)). The resulting solution was then diluted to 500 μl with lithium succinate buffer, and 50 μl aliquots were incubated at various temperatures for 7 minutes. Each sample was then cooled on ice for an additional 7 minutes. The acridinium ester coupled to unhybridized probe molecules was hydrolyzed by adding 150 μl of a solution containing 190 mM $Na_2B_4O_7$ (pH 7.6), 7% (v/v) TRITON®X-100 (polyoxyethylene p-t-octyl phenol) and 0.02% (w/v) gelatin, and the samples were heated at 60° C. for 10 minutes. The remaining (hybrid associated) chemiluminescence of each sample was determined in a LEADER® 50 Luminometer (MGM Instruments; Hamden, Conn.) by the automatic injection of a solution containing 0.1% v/v $H_2O_2$ in 0.001 M $HNO_3$ followed 0.5-2 seconds later by an injection of 200 μl of 1N NaOH. The resulting light emission was integrated over a 2 second interval.

Optical Method

Using the optical method, an identical set of oligonucleotide probes were synthesized having a linker arm but were not labeled with an acridinium ester. Four micrograms of each oligonucleotide probe were allowed to hybridize to 4 μg of the complementary RNA target for 60 minutes at 60° C. in 30 μl of a hybridization buffer containing 200 mM lithium hydroxide, 3 mM EDTA, 3 mM EGTA, 17% w/v lithium lauryl sulfate, and 190 mM succinic acid (pH 5.2). Following hybridization, 600 μl of the hybridization buffer was added, the sample split into two, and the melting behavior of each sample portion examined on a Beckman DU640 spectrophotometer equipped with a Micro $T_m$ analysis accessory. The temperature was varied 1° C. per minute for temperatures that were more than 10° C. either lower or higher than the $T_m$ and 0.5° C. per minute at intervals of 0.2° C. for all other temperatures. Changes in hypochromaticity were monitored and recorded as a function of temperature. Results are shown in Table 1 below.

TABLE 1

| Probe | Number of modified nucleotides | $T_m$ (chemiluminescent) | $T_m$ (optical) | $\Delta T_m$ |
|---|---|---|---|---|
| A | 0 | 68 | 72.4 | 0 |
| B | 26 | 90 | 91.2 | 22; 18.8 |
| C | 18 | 83 | 87.9 | 15; 15.5 |
| D | 8 | 72 | 76.4 | 4; 4 |
| E | 16 | nd | 84.2 | 11.6 | nd = not done

As shown in Table 1, the $T_m$ data generated using the chemiluminescent and optical methods agreed well with each other. The somewhat lower $T_m$ values observed with the chemiluminescent method can be attributed to the lower nucleic acid concentrations used in the chemiluminescent method versus the optical method. The data show that replacement of all of the deoxyribonucleotide residues of Probe A with 2'-O-methyl nucleotides (Probe B) resulted in probe:RNA target hybrids having a $T_m$ increased by about 20.4° C. Probes C, D and E exhibited $T_m$ increases of 15° C., 4° C., and 11.6° C., respectively. By calculating the effect on $T_m$ for each substitution of a 2'-O-methyl nucleotide, these data reveal that the $T_m$ of the 2'-O-methyl oligonucleotide:RNA target hybrid increases about 0.8° C. for every such replacement. This effect is approximately linear over the number of substitutions tested.

Example 2

Effect of 2'-Modified Nucleotides on $T_m$ of Probe:rRNA Hybrids

Three sets of oligonucleotide probes of different length and sequence were synthesized, and each set contained two oligonucleotides of identical base sequence. Probe F was 17 bases in length and included an acridinium ester label joined at a site located between a thymine base and an adenine base. Probe G was 18 bases in length and likewise included an acridinium ester label joined at a site located between a thymine base and an adenine base. Probe H was 20 bases in length and included an acridinium ester label joined at a site located between a thymine base and a guanine base.

Each set of probes contained one oligonucleotide consisting entirely of deoxyribonucleotides and another oligonucleotide containing only 2'-O-methyl nucleotides. Each probe was then hybridized to the corresponding ribosomal RNA, and the $T_m$ of the resulting hybrids determined by the chemiluminescent method described above. The results are shown in Table 2 below.

TABLE 2

| Probe | Length (bases) | $T_m$(deoxy) | $T_m$ (2'-O-methyl) | $\Delta T_m$ | $\Delta T_m$ per modified nucleotide |
|---|---|---|---|---|---|
| F | 17 | 63 | 81 | 18 | 1.05 |
| G | 18 | 66 | 78 | 12 | 0.66 |
| H | 20 | 62 | 75 | 13 | 0.65 |

The data confirm the results of Example 1, showing that replacement of a deoxyribonucleotide with a 2'-O-methyl nucleotide increases the $T_m$ of the resulting probe RNA target hybrid. Additionally, when calculated as the average of the three probes' increase in $T_m$ per modified nucleotide, the contribution of each modified nucleotide was an increase of 0.8° C. per modified nucleotide.

Example 3

Effect of 2'-Modified Nucleotides on $T_m$ of Probe:DNA Hybrids

In this Example, the effect of 2'-modification on probe:DNA targets was tested. Probe I, which contained varying amounts of 2'-O-methyl nucleotides, was hybridized to an exactly complementary DNA target of the same length and the melting behavior of the resultant hybrids examined by the chemiluminescent method described above. Probe I was 29 bases in length and included an acridinium ester label joined at a site located between a thymine base and a guanine base.

Probe I was designed to consist of: (i) all deoxyribonucleotides; (ii) all 2'-O-methyl nucleotides; and (iii) all 2'-O-methyl nucleotides except for four deoxyribonucleotides, which were positioned immediately on each side of the label attachment site. Results of the $T_m$ determination are shown in Table 3 below.

TABLE 3

| Probe | Number of 2'-O-methyl nucleotides | $T_m$ | $\Delta T_m$ per modified nucleotide |
|---|---|---|---|
| I | 0 | 69 | 0 |
| I | 29 | 77 | 0.28 |
| I | 21 | 75 | 0.29 |

As the data shows, replacement of deoxyribonucleotides with 2'-O-methyl nucleotides in Probes J and K caused the $T_m$ of the labeled probe:DNA target to increase approximately 0.3° C. per 2'-O-methyl residue.

A similar test was done using three sets of different oligonucleotides. Each set contained two oligonucleotides, one of the oligonucleotides containing deoxyribonucleotides and the other containing 100% 2'-O-methyl nucleotides, having identical base sequences.

Probe J was 16 bases in length and included an acridinium ester label joined at a site located between a thymine base and an adenine base. Probe K was 18 bases in length and likewise included an acridinium ester label joined at a site located between a thymine base and an adenine base. Probe L was 29 bases in length and included an acridinium ester label joined at a site located between a thymine base and a guanine base.

In each case the synthetic DNA targets were completely complementary to the probes. The results are shown in Table 4 below.

TABLE 4

| Probe | Number of 2'-O-methyl nucleotides | $T_m$ (optical method) | $\Delta T_m$ per modified nucleotide |
|---|---|---|---|
| J | 0 | 75.3 | 0 |
| J | 26 | 74.5 | −0.03 |
| K | 0 | 71.6 | 0 |
| K | 19 | 67.0 | −0.24 |
| L | 0 | 74 | 0 |
| L | 29 | 78.2 | 0.14 |

The data contained in Tables 3 and 4 demonstrates that the $T_m$ of DNA targets is increased to a significantly lesser degree than RNA targets when 2'-O-methyl substitutions are introduced into the probes.

Example 4

Analysis of the Stabilities of Different Types of Nucleic Acid Hybrids

To compare the relative stabilities of hybrids containing various combinations of DNA, RNA, and 2'-O-methyl nucleotide strands, the following acridinium ester-labeled oligonucleotide probes were hybridized to synthetic targets having a perfectly complementary base sequences (reading 5' to 3'):

```
SEQ ID NO:2:   gctcgttgcgggacttaacccaacat (DNA);

SEQ ID NO:3:   gcucguugcgggacuuaacccaacau
               (2'-O-methyl nucleotides);
and SEQ ID NO:7:   gcucguugcgggacuuaacccaacau (RNA).
```

As in Example 1, each probe was labeled with an acridinium phenyl ester compound joined to a linker arm attached to the probe between nucleotides 16 and 17 (reading 5' to 3'). The base sequences of the target sequences were as follows (reading 5' to 3'):

```
SEQ ID NO:1:   atgttgggttaagtcccgcaacgagc (DNA);

SEQ ID NO:8:   auguuggguuaagucccgcaacgagc
               (2'-O-methyl nucleotides);
and SEQ ID NO:9:   auguuggguuaagucccgcaacgagc (RNA).
```

The probes and target sequences contained 100% RNA (SEQ ID Nos. 7 and 9), 100% DNA (SEQ ID Nos. 1 and 2) or 100% 2'-O-methyl nucleotides (SEQ ID Nos. 3 and 8) in the combinations indicated in Table 5. The melting characteristics of each tested hybrid, as determined either using the chemiluminescent or the optical method, is shown in Table 5 below. More than one data point in the table indicates an independent, duplicate experiment.

TABLE 5

| Probe | Target | $T_m$ (chemiluminescent) | $T_m$ (optical) |
|---|---|---|---|
| DNA | RNA | 68, 67 | 73.3, 73.6, 73, 72.4 |
| RNA | RNA | 81 | nd |
| 2'-O-methyl nucleotides | RNA | 87, 90 | 91.2 |
| 2'-O-methyl nucleotides | 2'-O-methyl nucleotides | 91 | nd |
| DNA | DNA | nd | 75.5, 75.7, 75.1, 75.4 |
| 2'-O-methyl nucleotides | DNA | nd | 74.3, 74.8 | nd = no data

Thus, this experiment indicates that the stability of labeled probe:target hybrids follows the order: 2'-O-methyl/2'-O-methyl≧2'-O-methyl/RNA>RNA/RNA>DNA/DNA>2'-O-methyl/DNA>DNA/RNA

Example 5

Ability of Enhanced Stability of 2'-Modified Oligo:RNA Hybrids to Allow Specific RNA Targeting As indicated in Example 4, 2'-O-methyl:RNA hybrids are considerably more stable than 2'-O-methyl:DNA hybrids. To illustrate that this difference in stability can be exploited in a diagnostic assay to specifically detect RNA molecules over DNA molecules having an identical sequence (but with uracil in the RNA replacing thymine in the DNA), the following experiment was done.

The acridinium ester-labeled oligonucleotide probe of SEQ ID NO:3 (see Example 1 above) was allowed to hybridize to a completely complementary synthetic RNA target (SEQ ID NO:9) or DNA target (SEQ ID NO:1). Other than the fact that the oligonucleotide was labeled, hybridization and measurement of $T_m$ were otherwise as described in Example 1 under the heading Optical Method. The results are shown in Table 5 above and are further illustrated in FIG. 3.

Figure 3:
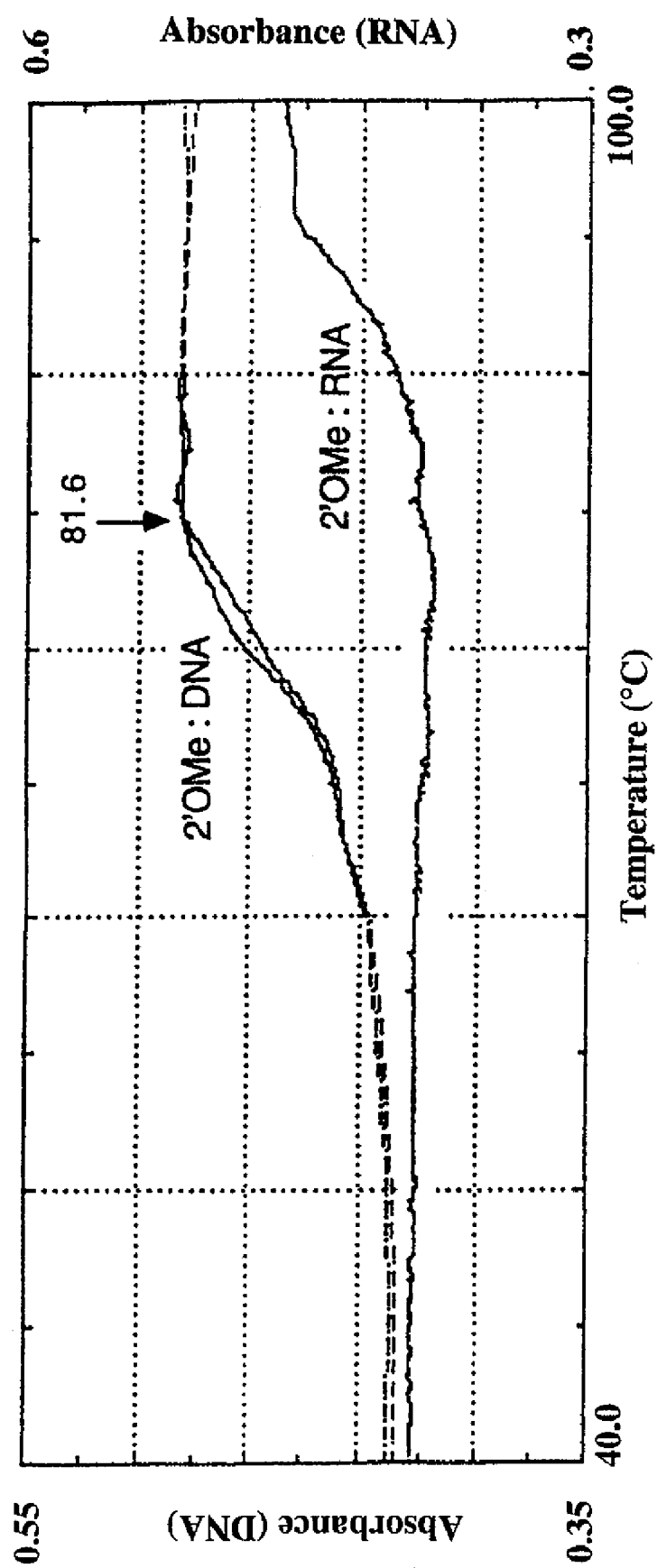
FIG. 3 shows the melting curve of a 2'-O-methyl oligonucleotide probe with either an RNA target or a DNA target (two independent experiments), where melting is shown as an increase in light absorbance at 260 nm (hyperchromatic shift).

As indicated in FIG. 3, at 81.6° C. the 2'-O-methyl oligonucleotide forms a detectable hybrid with the RNA target, but not with the DNA target. By contrast, Table 5 demonstrates that when a labeled DNA oligonucleotide of the same sequence is hybridized with the identical RNA or DNA targets, the resulting hybrids have substantially similar melting characteristics.

Thus, according to the aspect of the present invention demonstrated here, it is possible to specifically detect RNA targets in preference to DNA targets under easily determined hybridization conditions. Such methods may be used, as a nonexclusive example, to specifically detect various RNA species, such as mRNA, tRNA, or rRNA, without interference from the identical sequence existing in the genomic DNA of the organism being assayed. Such methods may be useful for applications including monitoring the rate of expression of a particular gene product. Other uses exploiting this ability of the 2'-modified oligonucleotides will be apparent to those of skill in the art.

Example 6

Effect of 2'-Modified Nucleotides on the Hybridization Kinetics of Oligonucleotides The effect of 2'-modified nucleotides on hybridization kinetics was illustrated using four different methods. The probe molecules used in this example were labeled with standard acridinium ester as described previously.

Figure 4:
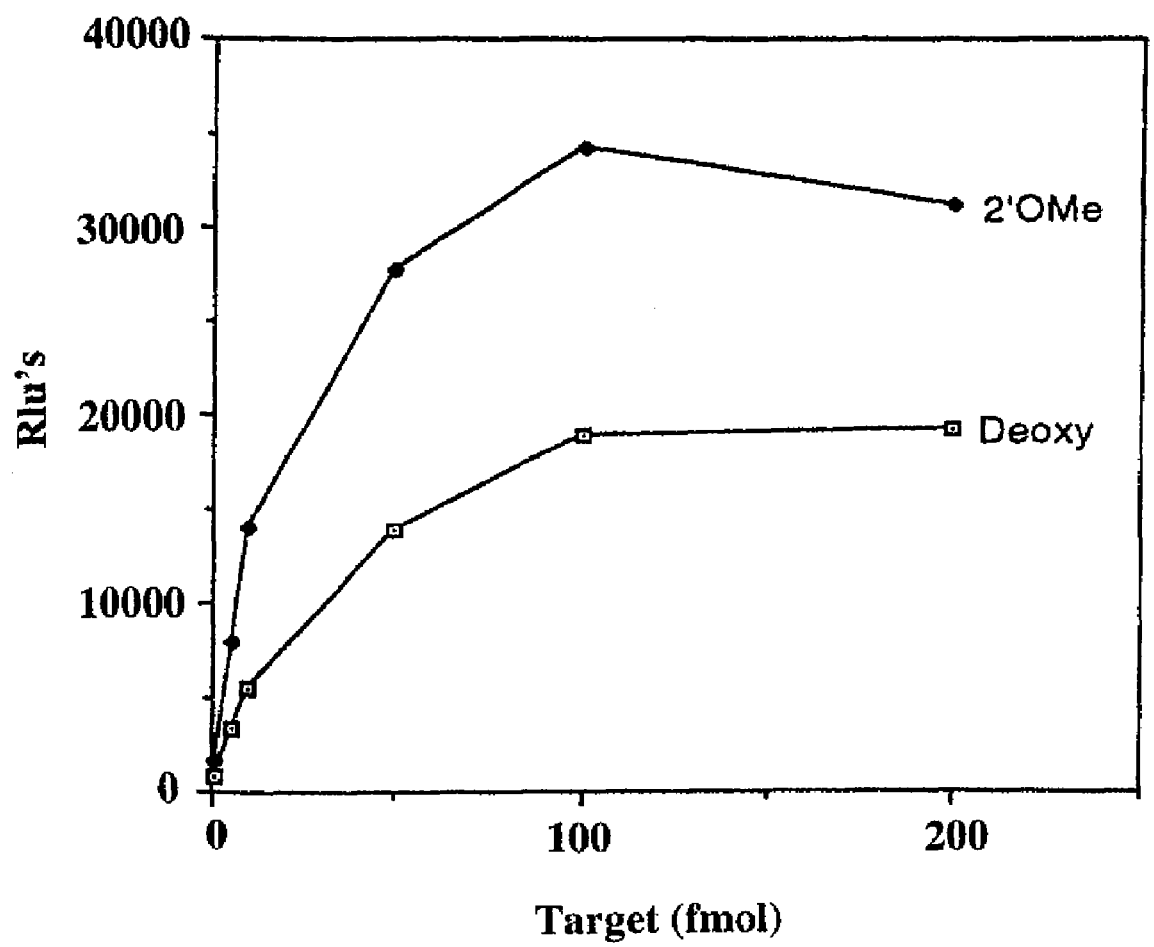
FIG. 4 shows hybridization of a single concentration of acridinium ester-labeled deoxy- or 2'-O-methyl oligonucleotides of identical base sequence to varying amounts of a fully complementary RNA target during a fixed time of hybridization.

(a) In the first approach, 2 fmol of an acridinium ester-labeled probe having the sequence of SEQ ID NO:2 or SEQ ID NO:3 (see Example 1 above) was hybridized to varying amounts of a completely complementary RNA target (SEQ ID NO:9) for a constant period of time, followed by differential hydrolysis and detection of the label. The hybridization was performed essentially as described in Example 1, under the heading Chemiluminescent Method, with the following differences. Varying amounts of RNA target were allowed to hybridize with the labeled probe at 60° C. for 45 minutes. FIG. 4 shows the results of this experiment, wherein the probe had either the DNA sequence of SEQ ID NO:2 (open boxes) or the 2'-O-methyl nucleotide sequence of SEQ ID NO:3 (closed diamond); these results are also tabulated in Table 6 below. The degree of hybridization is expressed in Relative Light Units (RLU), which is a measure of the number of photons emitted by the acridinium ester label.

TABLE 6

| Amount of Target (fmol) | RLU (DNA probe) | RLU (2'-O-methyl) |
|---|---|---|
| 1 | 855 | 1,739 |
| 5 | 3,394 | 8,009 |

TABLE 6-continued

| Amount of Target (fmol) | RLU (DNA probe) | RLU (2'-O-methyl) |
|---|---|---|
| 10 | 5,476 | 14,217 |
| 50 | 13,810 | 27,959 |
| 100 | 18,798 | 34,381 |
| 200 | 19,199 | 31,318 |

The results indicate that the hybridization rate, as a function of target concentration, is significantly increased when the probe contains 2'-O-methyl nucleotides rather than unmodified nucleotides. This holds true throughout the range of target concentrations studied. For comparison purposes, the initial slopes of these data are used to estimate the relative hybridization rates of deoxy- (slope=1.0) and 2'-O-methyl (slope=2.5) oligonucleotide probes.

Figure 5:
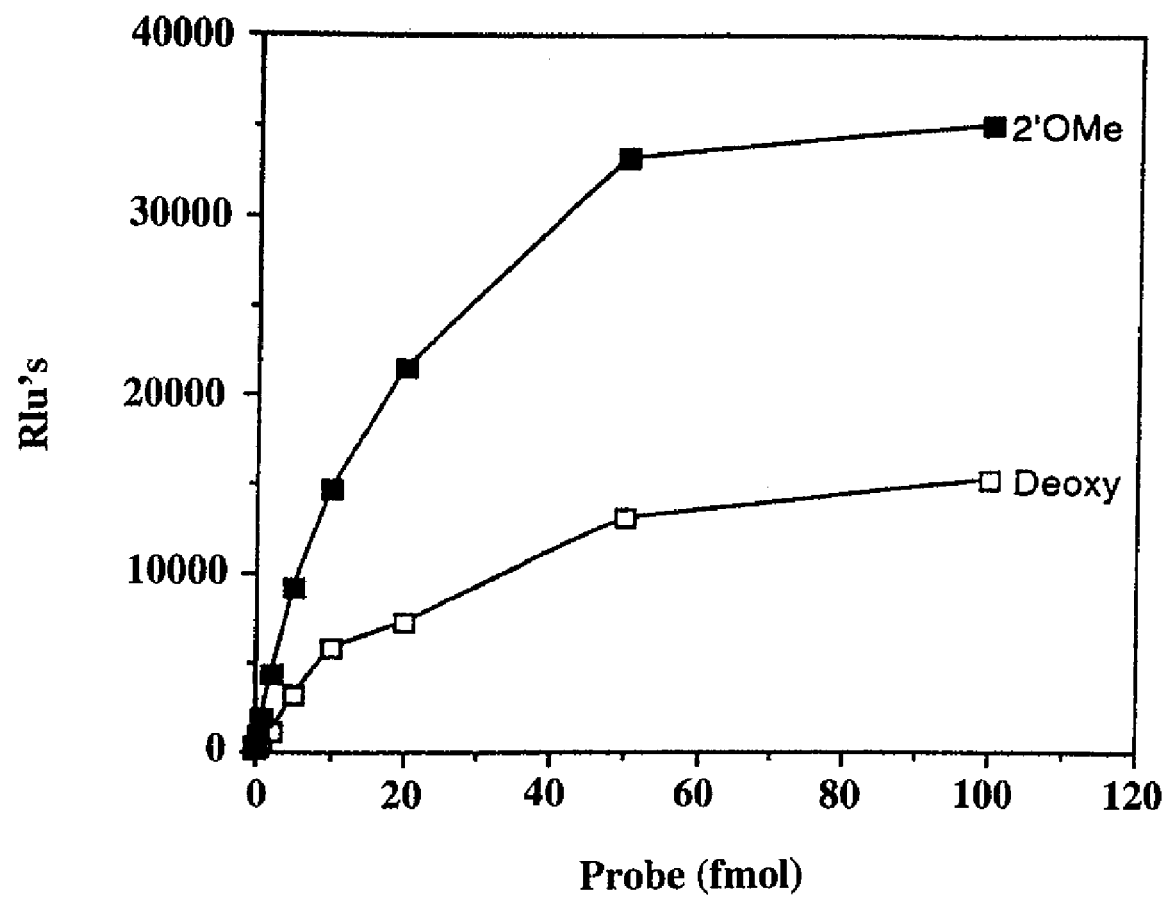
FIG. 5 shows hybridization of varying amounts of acridinium ester-labeled deoxy- or 2'-O-methyl oligonucleotides of identical base sequence to fixed amounts of a fully complementary RNA target during a fixed time of hybridization.

(b) In a second approach, a constant amount (2 fmol) of the same target used in a) above was hybridized to varying amounts of the perfectly complementary probe for a fixed amount of time. FIG. 5 shows the results of this experiment, wherein the probe had either the DNA sequence of SEQ ID NO:2 (open boxes) or the 2'-O-methyl nucleotide sequence of SEQ ID NO:3 (closed boxes). The hybridization and detection steps were the same as described in a) above, except that the hybridization reaction was carried out for 30 minutes rather than 45 minutes. The data are tabulated in Table 7 below.

TABLE 7

| Amount of Probe (fmoles) | RLU (DNA probe) | RLU (2'-O-methyl) |
|---|---|---|
| 0.2 | 99 | 346 |
| 0.5 | 309 | 966 |
| 1 | 690 | 1,973 |
| 2 | 1,206 | 4,356 |
| 5 | 3,227 | 9,184 |
| 10 | 5,801 | 14,615 |
| 20 | 7,289 | 21,515 |
| 50 | 13,080 | 33,236 |
| 100 | 15,223 | 34,930 |

Again, the results in this example indicate that the hybridization rate, which is a function of probe concentration, is significantly increased when the probe contains 2'-O-methyl nucleotides rather than unmodified nucleotides. The slopes of these plots are similar to those of FIG. 4, indicating that regardless of whether probe concentration or target concentration is varied, the difference in hybridization kinetics between 2'-O-methyl/DNA and DNA/DNA interactions remains the same. In this experiment, the initial slope of the reaction containing the DNA probe was 1.0 and of the reaction containing the 2'-O-methyl probe was 3.1.

Figure 6:
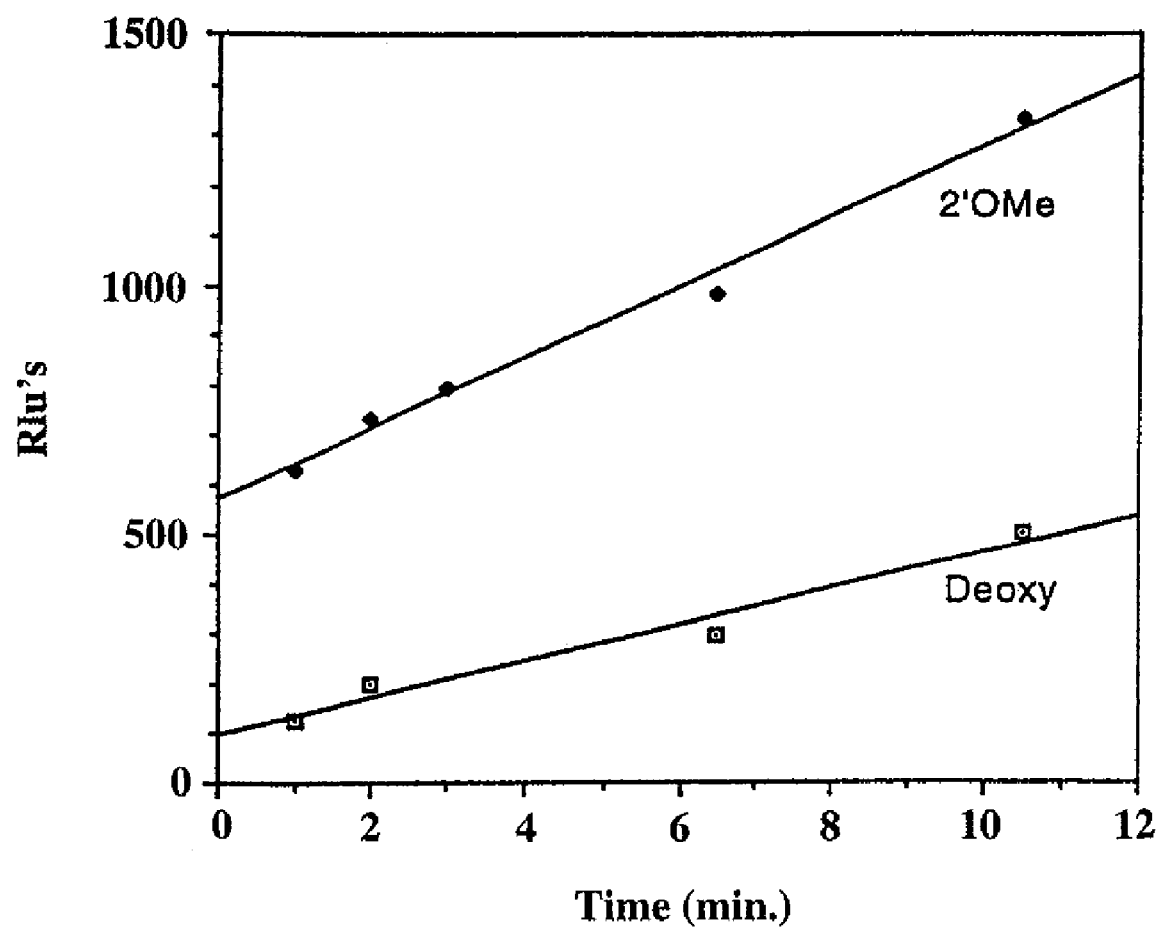
FIG. 6 shows hybridization of a fixed amount of acridinium ester-labeled deoxy- and 2'-O-methyl oligonucleotides of identical base sequence to a fixed amount of a fully complementary RNA target for various times of hybridization.

(c) As a third illustration of the ability of 2'-modified oligonucleotides to increase the rate of hybridization, fixed amounts of either modified or unmodified probe (1 fmol) and target (100 amol) were allowed to hybridize for varying amounts of time. The hybridization and detection protocols were otherwise the same as in b). FIG. 6 shows the results, wherein the probe had either the DNA sequence of SEQ ID NO:2 (open boxes) or the 2'-O-methyl nucleotide sequence of SEQ ID NO:3 (closed diamonds). The data were as follows in Table 8 below:

TABLE 8

| Time (minutes) | RLU (DNA probe) | RLU (2'-O-methyl) |
|---|---|---|
| 0 | 118 | 613 |
| 1 | 124 | 627 |
| 2 | 200 | 732 |
| 6.5 | 294 | 978 |
| 10.5 | 500 | 1331 |

Again, the relative rates of hybridization can be determined from the initial slopes of the curves (deoxy=1.0; 2'-O-methyl=2.2). In this experiment, the initial slope of the reaction containing the DNA oligonucleotide was 1.0, and the initial slope of the reaction containing the 2'-O-methyl oligonucleotide probe was 2.2-fold.

(d) The fourth method used to demonstrate the differences between the hybridization kinetics of 2'-modified and unmodified probes was a $C_o t$ analysis. Acridinium ester-labeled probes of SEQ ID Nos. 2 and 3 (see Example 1 above) were used. Either a fixed amount of probe and varied amounts of target ("probe excess") or a fixed amount of target and varying amounts of probe ("target excess") were allowed to hybridize at 60° C. for varying amounts of time. The fixed amount of either probe or target was 0.25 fmol and the variable amount of either probe or target included amounts in the range from 0.25 to 50 fmol. Hybridization was otherwise as indicated in Example 1, under the heading Chemiluminescent Method.

Differential hydrolysis of the unhybridized acridinium ester and detection of the hybridized probe was accomplished by adding 150 μl of 190 mM $Na_2B_4O_7$ (pH 7.6), 7% (v/v) TRITON® X-100 and 0.02% (w/v) gelatin to the sample, and heating the mixture to 60° C. for 10 minutes. Chemiluminescence was read in a luminometer, as described above. Percent maximal hybridization was defined as the ratio of the observed RLU value divided by the maximal RLU value observed when saturating amounts of probe or target were used in the hybridization reaction.

Figure 7:
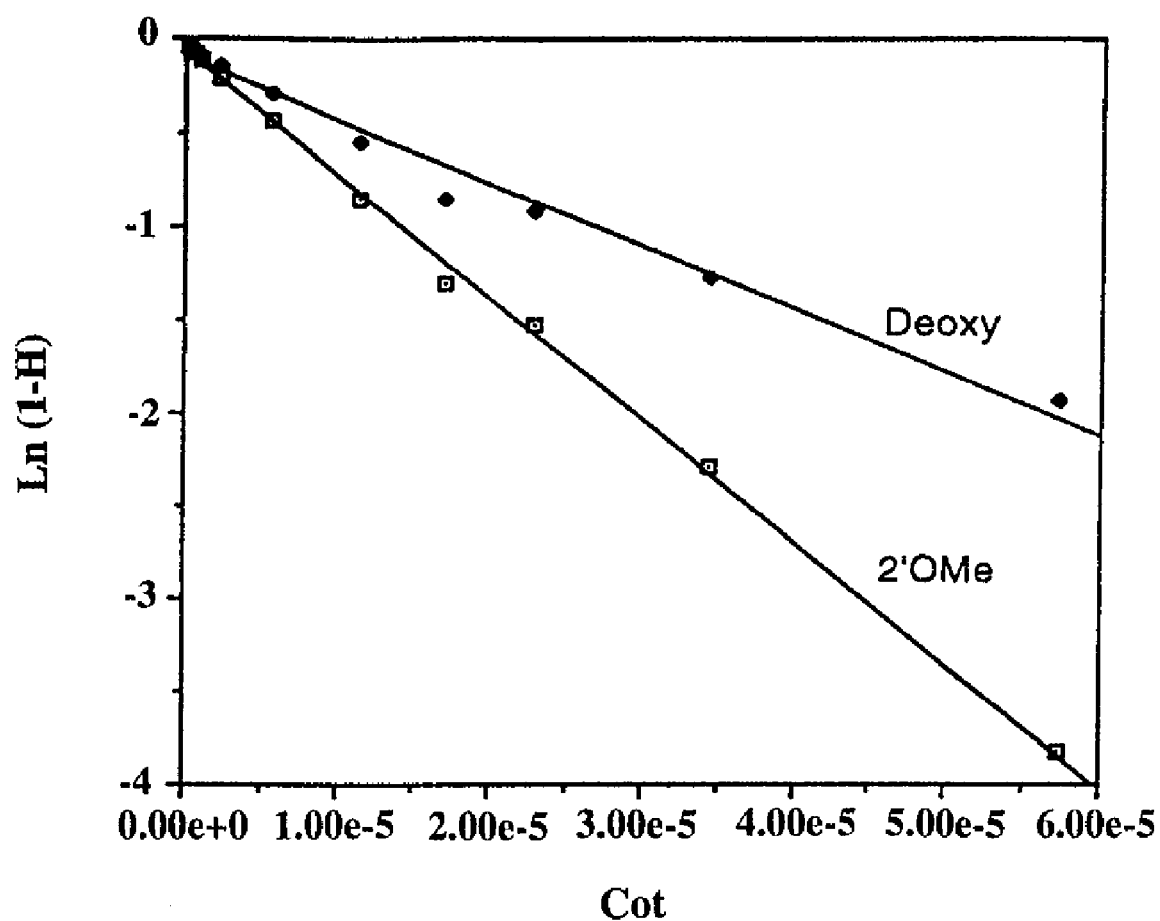
FIG. 7 shows hybridization of a DNA or 2'-O-methyl oligonucleotide probe to a fully complementary RNA target. The data are plotted according to the equation $\ln(1-H)=(k)(C_o t)$, where "H" is the percent hybridization, "k" is the hybridization rate constant, "$C_o$" is the concentration of probe, and "t" is time.

In the $C_o t$ plot shown in FIG. 7, the quantity ln (1−H) is plotted against the concentration of target times the hybridization time. The value H is defined as the percent hybridization of the probe at a particular target concentration after a particular time.

In this plot, the relative rates of hybridization of DNA and 2'-O-methyl oligonucleotide probes is given by the inverse of the relative ratios of $C_o t$ at 50% hybridization (ln(1−0.5); deoxy=1.0 and 2'-O-methyl=2.2).

A summary of the relative hybridization rates of an acridinium ester-labeled probe consisting entirely of deoxy- or 2'-O-methyl ribonucleotides determined by these four methods is summarized in Table 9. The data resulting from these experiments indicate that at 60° C. an oligonucleotide consisting entirely of 2'-O-methyl nucleotides hybridizes 2.3-fold faster than the corresponding deoxyribonucleotide probe.

TABLE 9

| Method | Probe (fmol) | Target (fmol) | Hybridization Time | Relative Rate (2'-O-methyl/deoxy-) |
|---|---|---|---|---|
| c | 0.05 | 1 | vary | 2.3 |
| c | 10 | 0.5 | vary | 2.3 |
| c | 0.1 | 1 | vary | 2.0 |
| c | 1 | 0.2 | vary | 1.6 |

TABLE 9-continued

| Method | Probe (fmol) | Target (fmol) | Hybridization Time | Relative Rate (2'-O-methyl/deoxy-) |
|---|---|---|---|---|
| c | 3 | 0.3 | vary | 2.9 |
| c | 10 | 1 | vary | 1.8 |
| b | vary | 1 | 30 | 2.6 |
| b | vary | 2 | 45 | 3.1 |
| a | 2 | vary | 45 | 2.5 |
| d | 0.25 | vary | 44 | 2.2 |

Example 7

Kinetic Analysis of Hybridization of 2'-Modified Oligonucleotides to Additional Targets To extend these hybridization rate comparisons to other probe and target sequences, Probe H of Example 2 above was synthesized entirely of either deoxy- or 2'-O-methyl nucleotides and hybridized to rRNA in the presence of helper probes. A $C_o t$ analysis was performed, as in Example 6(d). The results are shown in Table 10 below.

TABLE 10

| Probe | $C_o t_{1/2}$ | Relative Rates |
|---|---|---|
| deoxy | $0.3 \times 10^7$ | 1.00 |
| 2'-O-methyl | $8 \times 10^7$ | 3.75 |

In this Example, the probe consisting entirely of 2'-O-methyl nucleotides hybridized 3.75-fold faster than the deoxyribonucleotide probe of identical sequence. Thus, enhanced hybridization by acridinium ester-labeled probes containing 2'-O-methyl nucleotides does not appear to be limited to any particular probe or target sequence.

Example 8

Effect of Increased Temperature on Hybridization Rate of 2'-Modified Oligonucleotides As mentioned above, nucleic acid hybridization kinetics are accelerated by an increase in temperature. However, the advantages of this acceleration can be offset by the destabilizing effects of increased temperature on duplex formation, especially in diagnostic assays and nucleic acid amplification procedures employing relatively short oligonucleotides (between about 10 and about 50 bases in length). As shown below, the increased duplex stability provided by oligonucleotides modified as presently described can minimize this destabilizing effect, allowing the hybridization rate to be further increased by conducting the hybridization at a higher temperature than would otherwise possible. Thus, a cooperative effect on hybridization kinetics is provided by the modified oligonucleotides and the higher hybridization temperature.

An acridinium ester-labeled oligonucleotide probe having the sequence of SEQ ID NO:3 (see Example 1 above) was allowed to hybridize to a perfectly complementary RNA target of the same length as described above. The hybridization and $C_o t$ protocol were as described in Example 6(d), except that hybridization temperatures were either 60° C. or 70° C. As shown by the data in Table 11 below, raising the temperature of hybridization of the 2'-O-methyl oligonucleotide to its target from 60° C. or 70° C. caused the hybridization kinetics to be accelerated 1.5 fold.

TABLE 11

| Hybridization Temperature | $C_o t_{1/2}$ | Relative Hybridization Rates |
|---|---|---|
| 60° C. | $1.7 \times 10^{-5}$ | 1 |
| 70° C. | $1.1 \times 10^{-5}$ | 1.5 |

Example 9

Effect of Increasing Salt Concentration on Hybridization Kinetics of 2'-Modified Oligonucleotides Hybridization kinetics are also accelerated by increases in salt concentration. The following example illustrates the effect of various concentrations of salt, e.g., LiCl, on the hybridization kinetics of 2'-O-methyl nucleotides. An acridinium ester-labeled probe having the sequence of SEQ ID NO:3 (see Example 1 above) was allowed to hybridize, and a $C_o t$ analysis conducted, as described in Example 6(d) above, at 80° C. to an exactly complementary RNA target of the same length. Hybridization was performed at two different concentrations of LiCl. As shown in Table 12 below, increasing the salt concentration from 0.5 to 1.0 M LiCl enhanced the hybridization kinetics 2.9 fold.

TABLE 12

| LiCl Concentration | $C_o t_{1/2}$ | Relative Rates |
|---|---|---|
| 0.5 M | $0.72 \times 10^{-5}$ | 1 |
| 1.0 M | $0.25 \times 10^{-5}$ | 2.9 |

These results demonstrate that a two-fold increase in the salt concentration in a hybridization reaction leads to a 2.9-fold increase in the hybridization kinetics of modified oligonucleotides.

Example 10

Combined Effect on Hybridization Kinetics of Increasing Salt Concentration and Temperature To demonstrate the effect of simultaneously increasing the hybridization temperature and salt concentration on the hybridization kinetics of 2'-modified oligonucleotides, the following reactions were performed. An acridinium ester-labeled DNA oligonucleotide having the sequence of SEQ ID NO:2 and an acridinium ester-labeled oligonucleotide having the sequence of SEQ ID NO:3 (see Example 1 above) were each separately allowed to hybridize to an exactly complementary RNA target molecule in a $C_o t$ analysis. Hybridization conditions were as described in Example 6(d). Hybridization temperature and salt concentrations were as indicated in Table 13 below. The results were as follows:

TABLE 13

| Probe | Hybridization Temperature | LiCl Concentration | $C_o t_{1/2}$ | Relative Rates |
|---|---|---|---|---|
| DNA | 60° C. | 0.5 M | $1.9 \times 10^{-5}$ | 1 |
| 2'-O-methyl | 80° C. | 1.0 M | $0.22 \times 10^{-5}$ | 8.6 |

As the data indicate, at a hybridization temperature of 80° C. and in 1.0 M LiCi, the 2'-O-methyl oligonucleotide hybridized to its target at an 8.6-fold faster rate than did the corresponding DNA oligonucleotide at a temperature of 60° C. and salt concentration of 0.5 M LiCi.

Example 11

Comparison of Hybridization Rates of RNA, DNA and 2'-Modified Oligonucleotides Hybridizing to Complementary DNA and RNA Targets The relative hybridization rates of labeled RNA, DNA and 2'-O-methyl-containing oligonucleotides to completely complementary DNA and RNA targets were individually determined. Rate determination was performed as disclosed in either Example 6(c) or 6(d) above. The labeled oligonucleotides had the sequences of SEQ ID Nos. 2, 3 and 7 (see Example 1 above). The results are summarized in Table 14 below:

TABLE 14

| Probe | Target | Initial Slope | $C_o t_{1/2}$ | $T_m$ | Relative Rates |
|---|---|---|---|---|---|
| DNA | DNA | .0031, .0048 | — | 75.4 | 4.4 |
| RNA | DNA | — | — | 74.5 | — |
| 2'-O Me | DNA | .0014, .0014 | — | 74.6 | 1.6 |
| DNA | RNA | .0009 | — | 73.3 | 1 |
| RNA | RNA | — | $1.1 \times 10^{-5}$, $1.4 \times 10^{-5}$ | 81 | 2.8 |
| 2'-O Me | RNA | .004 | $.71 \times 10^{-5}$, $.89 \times 10^{-5}$ | 91.2 | 4.4 |

Experiments represented in Rows 1 through 4 were done as disclosed in Example 6(c) using 3 fmol of labeled probe and 0.3 fmol of target. The experiments represented in rows 5 and 6 were performed using the method described in Example 6(d). Where more than one result is indicated, each value corresponds to a different individual experiment.

The results of Table 14 demonstrate that substitution of deoxyribonucleotide residues with either 2'-OH residues (RNA) or 2'-O-methyl residues enhances the affinity, as well as the hybridization kinetics, of the probe to an RNA target. In contrast, substitution of deoxyribonucleotide residues with 2'-O-methyl residues does not enhance the affinity or the hybridization kinetics of the probe to a DNA target.

The results presented in Table 14 reveal that substitution of deoxyribonucleotide residues with 2'-O-methyl residues enhances the affinity and hybridization kinetics of a probe for an RNA target, but not a DNA target. However, these experiments do not eliminate the possibility that the acridinium ester label and/or the linker, by which it is attached to the probe, may be responsible for these hybridization rate characteristics. To show that the acridinium ester label and/or linker do not appreciably affect hybridization rates, the following experiment was performed.

An RNA probe of SEQ ID NO:7 labeled with acridinium ester (see Example 1 above) and containing a non-nucleotide linker by which the label was attached to the probe was allowed to hybridize to an exactly complementary target which consisted entirely of either 2'-O-methyl or deoxyribonucleotides. Hybridization and $C_o t$ analysis was done as Example 6(d). The results are expressed in Table 15 below.

TABLE 15

| Labeled Probe | Target | $C_o t_{1/2}$ | Relative Rates |
|---|---|---|---|
| RNA | DNA | $6.2 \times 10^{-5}$ | 1 |
| RNA | 2'-O-methyl | $2.3 \times 10^{-5}$ | 2.7 |

These data reveal that substitution of deoxyribonucleotides with 2'-O-methyl residues enhances the hybridization kinetics of an oligonucleotide lacking an acridinium ester and/or linker. Thus, the increased hybridization rate observed for 2'-O-methyl modified probes is not due to the presence of a label or linker arm, but is an intrinsic property of the 2'-O-methyl-modified oligonucleotide.

Example 12

Comparative Effect of Helper Probes on the Hybridization of Probes from DNA Probe Mixes and 2'-Modified Probe Mixes to an rRNA Target As disclosed in Hogan et al., U.S. Pat. No. 5,030,557, the hybridization of some probes to nucleic acids, especially those having a significant amount of secondary structure, is facilitated through the use of additional probes, termed "helper" probes. An example, though not the exclusive example, of a nucleic acid species having a high degree of secondary structure is ribosomal RNA (rRNA). Helper probes can help disrupt secondary structure which may mask the target region. The helper probe is usually targeted to a sequence region near, but preferably not overlapping with, the probe target sequence. In practice, helper probes are generally not labeled, and are usually used in a large molar excess. The effect of using helper probes on labeled probe hybridization is usually expressed as an increased $T_m$ and hybridization rate for the labeled probe:target hybrid.

The following experiments were performed to examine whether 2'-modified oligonucleotide probes have the same requirements for helper probes as do DNA probes when directed to given target regions containing a large amount of secondary structure. Two probe mixes were made. Each probe mix contained Probes F, G and H of Example 2 above. The oligonucleotides of one probe mix were made up of 100% 2'-O-methyl nucleotides, and the oligonucleotides of the other probe mix were composed entirely of deoxyribonucleotides. Where indicated, probe mixes included unlabeled DNA helper probes a, b, c, d, e and f having lengths of 33, 36, 41, 31, 29 and 40 bases, respectively.

Each helper probe was directed to rRNA base sequences close to the target site of one of the labeled probes. The degree of hybridization was measured using the hybridization protection assay (HPA), as described above. The results are reported in relative light units (RLU).

As shown in Table 16 below, in the absence of helper probes, DNA probe mixes hybridized poorly to rRNA. In contrast, when probe mixes employing 2'-O-methyl probes of identical sequence to the DNA probe mixes were hybridized to rRNA in the absence of helper probes, much higher levels of hybridization were observed. Additionally, when helper probes were used with both probe mixes, significantly greater hybridization of the probes to their target occurred with the 2'-modified oligonucleotide probe mixes. Because the hybridization of a DNA probe to an rRNA depends strongly on the presence of helper probes, while the hybridization of an identical 2'-O-methyl probe does not, 2'-O-methyl probes can efficiently hybridize to highly structured RNA molecules, such as ribosomal RNA, under conditions where DNA probes cannot.

TABLE 16

| Probe | Helpers | rRNA Concentration (amol) | RLU |
|---|---|---|---|
| DNA | no | 100 | 14 |
| DNA | yes | 100 | 3185 |
| 2'-O-methyl | no | 100 | 3116 |
| 2'-O-methyl | yes | 100 | 4332 |
| DNA | no | 1,000 | 68 |
| DNA | yes | 1,000 | 24,912 |
| 2'-O-methyl | no | 1,000 | 19,934 |
| 2'-O-methyl | yes | 1,000 | 33,584 |
| DNA | no | 10,000 | 730 |
| DNA | yes | 10,000 | 204,876 |
| 2'-O-methyl | no | 10,000 | 148,386 |
| 2'-O-methyl | yes | 10,000 | 256,940 |

The data in Table 16 further indicate that helper probes are not needed to facilitate probe binding when 2'-modified oligonucleotides are used. However, even greater sensitivity than seen before can be achieved in assays employing both helper probes and 2'-modified probes.

Example 13

Comparative Effect of Helper Probes on the Hybridization of a Single DNA Probe and a Single 2'-Modified Probe to an rRNA Target The results of the experiments described in Example 12 were generated using three separate labeled probes, either with or without the presence of the six helper oligonucleotides identified in Example 12. In this example, Probes F and H of Example 2, and consisting entirely of deoxyribo- or 2'-O-methyl nucleotides, were allowed to hybridize to target rRNA in the presence or absence of the indicated helper probes. Helper probes a, b, c and d of Example 12 above were used. Table 17 shows the hybridization characteristics of DNA and 2'-O-methyl oligonucleotides of Probe A. Table 18 shows the hybridization characteristics of DNA and 2'-O-methyl oligonucleotides of Probe H. Each labeled probe was tested in the presence or absence of the various helper probes and helper probe combinations indicated.

TABLE 17

| Probe | Target Concentration (amol) | Helper Probes | RLU |
|---|---|---|---|
| deoxy | 500 | None | 153 |
| deoxy | 500 | a | 5,600 |
| deoxy | 500 | b | 761 |
| deoxy | 500 | a and b | 9,363 |
| 2'-O-methyl | 500 | None | 14,537 |
| 2'-O-methyl | 500 | a | 16,556 |
| 2'-O-methyl | 500 | b | 15,586 |
| 2'-O-methyl | 500 | a and b | 16,868 |
| deoxy | 1,000 | None | 1,060 |
| deoxy | 1,000 | a | 14,782 |
| deoxy | 1,000 | b | 316 |
| deoxy | 1,000 | a and b | 26,877 |
| 2'-O-methyl | 1,000 | None | 28,874 |
| 2'-O-methyl | 1,000 | a | 23,201 |
| 2'-O-methyl | 1,000 | b | 16,269 |
| 2'-O-methyl | 1,000 | a and b | 44,510 |

TABLE 18

| Probe | Helper | RLU |
|---|---|---|
| deoxy | c | 870 |
| deoxy | d | 9,176 |
| deoxy | c and d | 47,745 |
| 2'-O-methyl | c | 88,292 |
| 2'-O-methyl | d | 69,943 |
| 2'-O-methyl | c and d | 98,663 |

Tables 17 and 18 demonstrate that the labeled DNA probes required helper oligonucleotides in order to effectively hybridize to their targets under the assay conditions. Additionally, Table 18 shows that the 2'-modified oligonucleotides hybridized to their targets to a greater degree in the absence of helper probes than the DNA oligonucleotides hybridized to the same target in the presence of the added helpers. Finally, 2'-O-methyl oligonucleotides exhibited even greater hybridization properties in the presence of helper oligonucleotides.

Example 14

Comparative Effect of Temperature on the Hybridization Properties of DNA Probes and 2'-Modified Probes with an rRNA Target in the Presence and Absence of Helper Probes The data presented in Example 13 indicates that 2'-O-methyl oligonucleotides hybridize to a detectable extent to RNA targets, even highly folded structures like rRNA, in the absence of helper probes. Nevertheless, helper probes can accelerate the hybridization of 2'-O-methyl oligonucleotides to highly structured RNA. To examine the effect of helper probes more closely, deoxy- and 2'-O-methyl oligonucleotide probes were hybridized to rRNA at different temperatures in the presence or absence of helper probes. Table 19 represents studies performed using acridinium ester-labeled probes having a nucleotide sequence of Probe F of Example 2 above and helper probes c and d of Example 12 above. Table 20 represents studies performed using acridinium ester-labeled probes having the sequence of SEQ ID NO:3 (see Example 1 above) and helper probes g and h having 41 and 32 bases, respectively.

TABLE 19

| Probe | Helpers | Temperature | $C_o t_{1/2}$ | Relative Rate |
|---|---|---|---|---|
| deoxy | Yes | 60° C. | $26.4 \times 10^{-5}$ | 1.3 |
| 2'-O-methyl | No | 60° C. | $35 \times 10^{-5}$ | 1 |
| 2'-O-methyl | Yes | 60° C. | $8.15 \times 10^{-5}$ | 4.3 |
| 2'-O-methyl | No | 75° C. | $12.9 \times 10^{-5}$ | 2.7 |
| 2'-O-methyl | Yes | 75° C. | $4.12 \times 10^{-5}$ | 8.5 |

TABLE 20

| Probe | Helpers | Temperature | $C_o t_{1/2}$ | Relative Rate |
|---|---|---|---|---|
| 2'-O-methyl | No | 60° C. | $7.46 \times 10^{-5}$ | 1 |
| 2'-O-methyl | Yes | 60° C. | $1.77 \times 10^{-5}$ | 4.2 |

These experiments demonstrate that at 60° and 75° C., helper probes enhanced the hybridization rates of the 2'-O-methyl probes to their targets 3.1-4.3 fold.

Example 15

Effect of 2'-Modified Nucleotides on the Hydrolysis Properties of Acridinium Ester-Labeled Probes As a further demonstration of the effect of modified oligonucleotides on the performance characteristics of diagnostic probe molecules, a number of additional experiments were performed. These experiments were based on the Applicant's preferred detection method employing the LPA detection assay. In accordance with one HPA format, a chemiluminescent acridinium ester is attached to a probe and the probe is hybridized to an analyte. Following hybridization, chemiluminescence associated with unhybridized probe is selectively destroyed by brief hydrolysis in borate buffer. Since probe:analyte molecules are not destroyed in this process, the remaining chemiluminescence of hybridized probe is a direct measure of the analyte present. In this application, those acridinium ester-labeled probes which hydrolyze faster when unhybridized than when in a probe-analyte hybrid complex are preferred. Hydrolysis of probe and hybrid is pseudo first order and can be characterized by the value t½, which is the time, measured in minutes, required to hydrolyze 50% of the acridinium ester attached to either probe or hybrid. Thus, probes which exhibit a large differential hydrolysis (DH) ratio (t½ (hybrid)/t½ (probe)) are highly desirable.

To examine the effect of modified oligonucleotides on the hydrolysis properties of acridinium ester-labeled probes, four sets of probes were constructed, each set having a distinct nucleotide base sequence and each member of a set having identical nucleotide base sequences. Each set of probes contained one probe consisting entirely of unmodified nucleotides and another probe consisting entirely of 2'-O-methyl nucleotides. The probes used were Probes A and B of Example 1 above and Probes F, G and H of Example 2 above. OH ratios of each probe to an exactly complementary RNA target were determined as described above, for example, in Example 1. As summarized in Table 21 below, unhybridized probes containing deoxy- or 2'-O-methyl nucleotides hydrolyzed at very similar rates.

TABLE 21

|   | Probe | Ribonucleotides | t½ (Probe) | t½ (Hybrid) | DH |
|---|---|---|---|---|---|
| A | A | deoxy | .81 | 49.1 | 60.3 |
|   | B | 2'-O-methyl | .63 | 77.2 | 123.5 |
| B | F | deoxy | .36 | 20.79 | 7.74 |
|   | F | 2'-O-methyl | .89 | 75.25 | 4.55 |
| C | H | deoxy | .69 | 17.26 | 25 |
|   | H | 2'-O-methyl | .76 | 44.7 | 58.8 |
| D | G | deoxy | .62 | 25.67 | 41.4 |
|   | G | 2'-O-methyl | .81 | 23.55 | 29.7 |

In contrast, the modified probe:target hybrid-associated label for three of the sequences was approximately 2-fold more resistant to hydrolysis than in the otherwise identical unmodified probe:target hybrid. In one case, in which the probe contained an ATAT sequence surrounding the acridinium ester linker, the DH ratio was decreased 1.4-fold for the modified probe target hybrid-associated label.

Example 16

Effect of Position of 2'-Modified Nucleotides on the Hydrolysis Properties of Acridinium Ester-Labeled Probe To examine whether modified nucleotides must be close to the site of label attachment to enhance the DH behavior of acridinium ester, acridinium ester-labeled probes containing clusters of 2'-O-methyl nucleotides at different positions relative to the acridinium ester linker site were hybridized to a complementary RNA target. Labeled Probes A, B, C and D of Example 1 were used for this example. As shown in Table 22 below, the measurements reveal that 4 contiguous 2'-O-methyl nucleotides on either side of the acridinium ester linker site are sufficient to enhance the DH behavior of an acridinium ester-labeled probe as much as a probe consisting entirely of 2'-O-methyl nucleotides. More than one data point in the table indicates independent, duplicate experiments.

TABLE 22

| Probe | t½ (Probe) | t½ (Hybrid) | DH |
|---|---|---|---|
| A | .82, .8 | 48.7, 43.2 | 59.7, 54 |
| B | .76, .6 | 90, 77.6 | 118.3, 129 |
| C | .74 | 49.8 | 67.3 |
| D | .44 | 81.4 | 185 |

Example 17

Effect of Temperature on the Hydrolysis Properties of 2'-Modified Acridinium Ester-Labeled Probes As mentioned above, because of their higher thermal stability, the modified oligonucleotides of the present invention are able to hybridize to a target nucleic acid at a higher temperature than unmodified oligonucleotides. At such higher temperatures, the hybridization rate, as well as the rate of other reactions, would be expected to increase. Among such other reactions is the rate of hydrolysis of acridinium ester labels. Because Applicant's preferred detection method employs the Hybridization Protection Assay (HPA), described and incorporated by reference above, the following experiment was performed to determine whether benefits to the diagnostic assay conferred by an increase in hybridization rate would be offset by a decrease in the DH ratios of hybrid-associated and unassociated acridinium ester labels at this higher temperature.

An acridinium ester-labeled probe consisting entirely of 2'-O-methyl nucleotides was allowed to hybridize to a complementary RNA target at 60°, 70° and 80° C. Hybridization conditions were as otherwise as described previously.

As summarized in Table 23 below, at 70° C. and 80° C. acridinium ester-labeled probes containing 2'-O-methyl nucleotides exhibited DH ratios comparable to acridinium ester-labeled probes containing deoxyribonucleotides at 60° C. Thus, elevated temperature may be used in diagnostic assays employing the methods and compositions of the present invention without a detectable decrease in assay sensitivity due to degradation of the label.

TABLE 23

| Temp (° C.) | Probe | t½ (Probe) | t½ (Hybrid) | DH |
|---|---|---|---|---|
| 60 | deoxy | .82 | 48.7 | 59.7 |
| 60 | 2'-O-methyl | .76 | 90 | 118 |
| 70 | 2'-O-methyl | .42 | 25.7 | 61.3 |
| 80 | 2'-O-methyl | .25 | 10.1 | 40.8 |

Example 18

Effect of 2'-Modified Nucleotides on the Hydrolysis Properties of Various Acridinium Ester-Labeled Probes The foregoing experiments were conducted using standard acridinium ester as the detectable chemiluminescent label. To examine whether the differential hydrolysis behavior of labels other than standard acridinium ester is enhanced by $T_m$-enhancing modified nucleotides, probes containing either deoxyribonucleotides (SEQ ID NO:2) or 2'-O-methyl nucleotides (SEQ ID NO:3) were labeled in exactly the same manner and position (see Example 1 above) with standard acridinium ester, o-diBr acridinium ester, 2-Me acridinium ester, napthyl-acridinium ester, o-F acridinium ester, 2,7-diisopropylacridinium ester, or mixture of 1- and 3-Me acridinium ester, and their DH behavior examined. See FIG. 1 for examples of acridinium esters. As summarized in Table 24 below, the use of modified nucleotide probes resulted in an increase in the DH ratio for all the acridinium ester derivatives tested by 1.1-6 fold.

TABLE 24

| Label | Probe | t½ (Probe) | t½ (Hybrid) | DH |
|---|---|---|---|---|
| Standard Acridinium ester | deoxy | .81 | 49.1 | 60.3 |
| Standard Acridinium ester | 2'-O-methyl | .63 | 77.2 | 123.5 |
| o-diBr-acridinium ester | deoxy | .94 | 23.44 | 24.94 |
| o-diBr-acridinium ester | 2'-O-methyl | 1.01 | 66.65 | 66 |
| 2-Me-acridinium ester | deoxy | .84 | 73.6 | 87.62 |
| 2-Me-acridinium ester | 2'-O-methyl | .78 | 101.8 | 130.5 |
| Napthyl acridinium ester | deoxy | .72 | 14.45 | 20.07 |
| Napthyl acridinium ester | 2'-O-methyl | .57 | 53.4 | 93.68 |
| o-F acridinium ester | deoxy | .93 | 53.3 | 57.3 |
| o-F acridinium ester | 2'-O-methyl | 1.03 | 78.75 | 76.46 |
| 2,7-diisopropyl acridinium ester | deoxy | 1.23 | 38.55 | 31.3 |
| 2,7-diisopropyl acridinium ester | 2'-O-methyl | 0.8 | 43.90 | 54.9 |
| Mixture of 1- and 3-Me acridinium ester | deoxy | .97 | 12.6 | 129.8 |
| Mixture of 1- and 3-Me acridinium ester | 2'-O-methyl | 1.24 | 149.5 | 120.6 |

Example 19

Relationship Between the Hybridization Kinetics and the Number of 2'-Modified Nucleotides Contained in a Probe Sequence To examine the relationship between hybridization kinetics and the number of 2'-O-methyl nucleotides within a probe sequence, Probes A, B, D and E of Example 1 were synthesized, as well as the following probe sequences (reading 5' to 3') labeled in the same manner and location as the probes of Example 1 with an acridinium phenyl ester compound:

SEQ ID NO:10: gctcgttgcgggacttaacccaacat (Probe M); and

SEQ ID NO:11: gctcgttgcgggacttaacccaacat (Probe N).

The bolded nucleotides represent 2'-O-methyl nucleotides. The results are summarized in Table 25 below.

TABLE 25

| 2'-O-methyl Residues | $C_o t$ (Exp 1) | $C_o t$ (Exp 2) | $C_o t$ (Exp 3) | Relative Rate |
|---|---|---|---|---|
| 0 | $1.87 \times 10^{-5}$ | $2.2 \times 10^{-5}$ | — | 1 |
| 2 | — | — | $1.13 \times 10^{-5}$ | 1.8 |
| 4 | $1.28 \times 10^{-5}$ | — | $0.93 \times 10^{-5}$ | 1.8 |
| 8 | — | $0.93 \times 10^{-5}$ | $0.86 \times 10^{-5}$ | 2.3 |
| 16 | — | — | $0.96 \times 10^{-5}$ | 2.1 |
| 25 | $0.91 \times 10^{-5}$ | $1 \times 10^{-5}$ | $0.84 \times 10^{-5}$ | 2.2 |

As summarized above, as few as 8 2'-O-methyl nucleotides (Probe D)—4 on each side of the acridinium ester linker site—were sufficient to accelerate the hybridization rate of an acridinium ester probe to the same level of a probe consisting almost entirely of 2'-O-methyl nucleotides (Probe B). In contrast, the $T_m$ of a probe containing four 2'-O-methyl nucleotides on each side of the acridinium ester linker site is lower than the $T_m$ of a probe:target hybrid in which the probe contains additional 2'-O-methyl nucleotides. Thus, according to the present invention it is possible to optimize, or "tune", the performance of an acridinium ester labeled probe with respect to its hybridization rate, differential hydrolysis, and melting properties. For example, an acridinium ester-labeled probe containing four 2'-O-methyl nucleotides on either side of the acridinium ester linker site will have its hybridization rate and differential hydrolysis properties maximally optimized, while a hybrid containing this probe will exhibit only a small increase in its melting temperature.

As substantially contiguous 2'-O-methyl nucleotides are added to replace deoxyribonucleotides in the labeled probe, the hybridization rate and differential hydrolysis properties of the probe:target hybrid will remain substantially constant while its $T_m$ will continue to increase. The ability to increase, incrementally, the influence of a probe on the $T_m$ of a probe:target hybrid allows one to adjust the specificity of a probe so as not to cross-react with closely related sequences, as shown in Table 25 above.

Example 20

Effect of Propyne-Modifications on the $T_m$ of Probe:Target Hybrids

In order to illustrate the general usefulness of the compositions and methods of the present invention in the diagnostic application of nucleic acid hybridization technology, oligonucleotides were constructed having a modification other than a 2'-modification to the ribofuranosyl moiety, but which also caused an increase in the binding affinity of a probe for its target. In this example, oligonucleotides were synthesized containing two nucleotides modified at the nitrogenous base. Specifically, N-diisobutylaminomethylidene-5-(1-propynyl)-2'-deoxycytidine; (a cytidine analog) and 5-(1-propynyl)-2'-deoxyuridine) (a thymidine analog). These nucleotide analogs are commercially available, for example, from Glen Research in Sterling, Va.

As a first consideration, probes having 22 bases and an acridinium-ester attached at a site located between a thymine base and a guanine base in Probes O and P and between two thymine bases in Probe Q, but containing varying numbers of propyne-modified nucleotides, were hybridized to target rRNA in the presence of helper probes to examine the effect of the modification on the $T_m$ of acridinium ester hybrids. Probe O contained no propyne modifications. Probe Q contained two propyne modifications, one directly adjacent to each side of the label attachment site. Probe P contained 11 propyne modifications, including four contiguous modifications directly adjacent and 5' to the label attachment site and seven modifications located at bases spaced 3, 4, 6, 9-11 and 14 bases away from and 3' to the label attachment site.

Hybridization and $T_m$ determinations were performed as described above using detection of acridinium ester-labeled hybrids. As summarized below in Table 26, these data indicate that the $T_m$ of the oligonucleotide, when hybridized to an RNA target, increased an average of 1° C. for every replacement of a pyrimidine with a propyne-substituted pyrimidine.

TABLE 26

| Probe | Propyne Residues | $T_m$ (chemiluminescent) | ΔT/Propyne |
|---|---|---|---|
| O | 0 | 71 | — |
| P | 2 | 72 | 0.5 |
| Q | 11 | 82 | 1.0 |

Example 21

Effect of Propyne Modifications on the Hybridization Kinetics of Oligonucleotides To examine the effect of propyne groups on the hybridization kinetics of oligonucleotides, the rate of hybridization of the propyne-labeled probes of Example 20 to RNA were examined by $C_ot$ analysis, as described in Example 6. As summarized below in Table 27, the probe containing two propyne groups (Probe 0) hybridized at the same rate as the probe containing no propyne groups (Probe P), while the probe containing 11 propyne groups (Probe Q) hybridized 1.9-fold faster.

TABLE 27

| Probe | $C_ot_{1/2}$ | Relative Rate |
|---|---|---|
| O | $0.75 \times 10^{-5}$ | 1 |
| P | $0.81 \times 10^{-5}$ | 0.93 |
| Q | $0.39 \times 10^{-5}$ | 1.9 |

These data support the generality of the present invention by demonstrating that modifications to oligonucleotides which result in an increased $T_m$ also cause the rate of hybridization of the modified oligonucleotide to its target to increase compared to an unmodified oligonucleotide of the same base sequence. Moreover, this example also demonstrates that such modifications may occur in the nitrogenous base moiety as well as the sugar moiety. Those of skill in the art will recognize that such modifications may also occur in the internucleotide linkage as well.

Although the foregoing disclosure describes the preferred embodiments of the present invention, Applicant should not be limited thereto. Those of skill in the art to which this invention applies will comprehend additional embodiments in light of this disclosure. Moreover, additional embodiments are within the claims which conclude this specification and their equivalents.

What is claim is:

1. A method of amplifying and detecting the presence of a target nucleic acid in a reaction mixture, the method comprising the steps of:
   (a) performing a transcription-based amplification reaction to produce a transcription product having an RNA sequence contained within or complementary to a RNA or equivalent DNA sequence of the target nucleic acid; and
   (b) detecting the transcription product as an indication of the presence of the target nucleic acid in the reaction mixture, the transcription product forming a hybridization complex with a target binding region of a probe molecule, wherein the target binding region comprises at least one 2'-O-methyl ribonucleotide.

2. The method of claim 1, wherein the target binding region comprising a cluster of at least 4 contiguous 2'-O-methyl ribonucleotides.

3. The method of claim 1, wherein the target binding region consists of 2'-O-methyl ribonucleotides.

4. The method of claim 1, wherein the probe molecules comprises a conjugate molecule.

5. The method of claim 2, wherein the probe molecules comprises a conjugate molecule joined to the target binding region at a site located within the cluster of 2'-O-methyl ribonucleotides.

6. The method of claim 1, wherein the probe molecules is from 10 to and 100 nucleotide bases in length.

7. The method of claim 1, wherein the probe molecules is from 10 to 16 nucleotide bases in length.

8. The method of claim 1, wherein the label is a chemiluminescent or a fluorescent agent.

9. The method of claim 1, wherein the probe molecules comprise self-complementary regions which include the at least one 2'-O-methyl ribonucleotide.

10. The method of claim 1, wherein the transcription product comprises a structured region, and wherein the target binding region forms a hybridization complex with the structured region in step (b).

11. The method of claim 1 further comprising the step of quantifying the amount of target nucleic acid present in the reaction mixture.

12. The method of claim 1, wherein the amplification reaction is a transcription-mediated amplification reaction.

* * * * *